US012735404B2

(12) United States Patent
Jang et al.

(10) Patent No.: US 12,735,404 B2
(45) Date of Patent: Sep. 15, 2026

(54) INDIRUBIN DERIVATIVES HAVING HETEROBICYCLIC MOIETIES AND THE USE THEREOF

(71) Applicant: Pelemed Co., Ltd., Seoul (KR)

(72) Inventors: Soo Yeon Jang, Seoul (KR); Myung Jin Kim, Seoul (KR); Jin Hee Park, Seoul (KR); So Deok Lee, Gwangju (KR); Su Jin Oh, Seoul (KR); Eun Ji Lee, Seoul (KR); Yong Chul Kim, Gwangju (KR); Woo Chan Kim, Daejeon (KR); Je Heon Lee, Daejeon (KR)

(73) Assignee: Pelemed Co., Ltd., Gwangju (KR)

( * ) Notice: Subject to any disclaimer, the term of this patent is extended or adjusted under 35 U.S.C. 154(b) by 623 days.

(21) Appl. No.: 18/040,102

(22) PCT Filed: Dec. 23, 2022

(86) PCT No.: PCT/KR2022/021194
§ 371 (c)(1),
(2) Date: Jan. 31, 2023

(87) PCT Pub. No.: WO2023/153630
PCT Pub. Date: Aug. 17, 2023

(65) Prior Publication Data

US 2024/0010635 A1 Jan. 11, 2024

(30) Foreign Application Priority Data

Feb. 14, 2022 (KR) ........................ 10-2022-0019138

(51) Int. Cl.
*C07D 403/14* (2006.01)
*A61P 35/00* (2006.01)
(Continued)

(52) U.S. Cl.
CPC ............ *C07D 403/14* (2013.01); *A61P 35/00* (2018.01); *C07D 471/18* (2013.01); *C07D 487/10* (2013.01)

(58) Field of Classification Search
CPC ...... C07D 403/14; C07D 471/18; A61P 35/00
(Continued)

(56) References Cited

U.S. PATENT DOCUMENTS 11,370,779 B2 * 6/2022 Kim et al. ........... C07D 403/04
2020/0270229 A1 * 8/2020 Kim et al. ........... C07D 403/04

FOREIGN PATENT DOCUMENTS

KR 10-2021-0071858 A 6/2021
RU 2410387 C2 1/2011
(Continued)

OTHER PUBLICATIONS

Burkhard JA, Wagner B, Fischer H, Schuler F, MÃ1/4ller K, Carreira EM. Synthesis of azaspirocycles and their evaluation in drug discovery. Angew. Chem., Int. Ed. Apr. 1, 2010;49(20):3524-7. (Year: 2010).*
(Continued)

*Primary Examiner* — Jeffrey S Lundgren
*Assistant Examiner* — Heather Dahlin
(74) *Attorney, Agent, or Firm* — Servilla Whitney LLC

(57) ABSTRACT

The present invention relates to novel indirubin derivatives having heterobicyclic moieties, and use thereof as fms-like tyrosine kinase 3 (FLT3) and rearranged during transfection (RET) kinase inhibitors. The compound of the present invention effectively inhibits the activity of FLT3 and RET kinases, and thus may be useful for preventing or treating mutant FLT3 and mutant RET-related diseases, particularly acute myeloid leukemia.

15 Claims, 2 Drawing Sheets

(51) Int. Cl.
*C07D 471/18* (2006.01)
*C07D 487/10* (2006.01)

(58) Field of Classification Search
USPC .......................................................... 514/414
See application file for complete search history.

(56) References Cited

FOREIGN PATENT DOCUMENTS

| | | | |
|---|---|---|---|
| WO | 2007099402 | A2 | 9/2007 |
| WO | 2014153023 | A1 | 9/2014 |
| WO | 2019088677 | A1 | 5/2019 |

OTHER PUBLICATIONS

Burkhard JA, Wagner B, Fischer H, Schuler F, Maller K, Carreira EM. Synthesis of azaspirocycles and their evaluation in drug discovery. Angew. Chem., Int. Ed. Apr. 1, 2010;49(20):3524-7. (Year: 2010).*

Nam S, Scuto A, Yang F, Chen W, Park S, Yoo HS, Konig H, Bhatia R, Cheng X, Merz KH, Eisenbrand G. Indirubin derivatives induce apoptosis of chronic myelogenous leukemia cells involving inhibition of Stat5 signaling. Molecular oncology. Jun. 1, 2012;6(3):276-83. (Year: 2012).*

Karadsheh R, Meuser ME, Cocklin S. Composition and orientation of the core region of novel HIV-1 entry inhibitors influences metabolic stability. Molecules. Mar. 21, 2020;25(6):1430. (Year: 2020).*

Zhang G, Howe M, Aldrich CC. Spirocyclic and bicyclic 8-nitrobenzothiazinones for tuberculosis with improved physicochemical and pharmacokinetic properties. ACS Medicinal Chemistry Letters. Feb. 23, 2019;10(3):348-51. (Year: 2019).*

Burkhard JA, Wagnen B, Fischer H, Schulen F, Maller K, Carreira EM. Synthesis of azaspirocycles and their evaluation in drug discovery. Angew. Chem., Int. Ed. Apr. 1, 2010;49(20):3524-7. (Year: 2010).*

Karadsheh R, Meuser ME, Cocklin S. Composition and orientation of the core region of novel HIV-1 entry inhibitors influences metabolic stability. Molecules. Mar. 2, 20201;25(6): 1430. (Year: 2020).*

Zhang G, Howe M, Aldrich CC. Spirocyclic and bicyclic 8-nitrobenzothiazinones for tuberculosis with improved physicochemical and pharmacokinetic properties. ACS Medicinal Chemistry Letters. Feb. 2, 20193;10(3):348-51. (Year: 2019).*

Korean Office Action in Serial No. 10-2022-0019138 dated Mar. 6, 2024, 5 pages.

Machine Translation of Korean Office Action in Serial No. 10-2022-0019138 dated Mar. 6, 2024, 5 pages.

Machine Translation of KR 10-2021-0071858 dated Jun. 16, 2021, 38 pages.

Abu-Duhier, F. M., et al., "FLT3 internal tandem duplication mutations in adult acute myeloid leukaemia define a high-risk group", British Journal of Haematology, Oct. 2000., 111(1): 190-5 (Abstract).

Birg, Francoise , et al., "Expression of the FMS/KIT-Like Gene FLT3 in Human Acute Leukemias of the Myeloid and Lymphoid Lineages", Blood, vol. 80, No. 10 (Nov. 15, 1992): pp. 2584-2593.

Brown, P., et al., "FLT3 Inhibitors—A paradigm for the development of targeted therapeutics for paediatric cancer", European Journal of Cancer, Paediatric Update, vol. 40, Issue 5, p. 707-721, Mar. 2004 (Abstract).

Carow, Catherine E., et al., "Expression of the Hematopoietic Growth Factor Receptor FLT3 (STK-UFIk2) in Human Leukemias", Blood, vol. 87, No. 3 (Feb. 1, 1996): pp. 1089-1096.

Gaboriaud-Kolar, Nicolas , et al., "Natural-Based Indirubins Display Potent Cytotoxicity toward Wild-Type and T315I-Resistant Leukemia Cell Lines", J. Nat. Prod. 2016, 79, 2464-2471.

Ger, Marija , et al., "Proteomic Identification of FLT3 and PCBP3 as Potential Prognostic Biomarkers for Pancreatic Cancer", Anticancer Research 38: 5759-5765 (2018).

Jeong, Pyeonghwa , et al., "Discovery of orally active indirubin-3'-oxime derivatives as potent type 1 FLT3 inhibitors for acute myeloid leukemia", European Journal of Medicinal Chemistry 195 (2020) 112205, 17 pages.

Kohno, Takashi , et al., "KIF5B-RET fusions in lung adenocarcinoma", Nat Med.; 18(3): 375-377.

Matsubara, Daisuke , et al., "Identification of CCDC6-RET Fusion in the Human Lung Adenocarcinoma Cell Line, LC-2/ad", Journal of Thoracic Oncology • vol. 7, No. 12, Dec. 2012, pp. 1872-1876.

Mulligan, Lois M., "Nature Reviews Cancer", 14(3), 173-186 (2014) (Abstract).

Rudat, S. , et al., "RET-mediated autophagy suppression as targetable co-dependence in acute myeloid leukemia", Leukemia 32, 2189-2202 (2018) (Abstract).

Yamamoto, Yukiya, et al., "Activating mutation of D835 within the activation loop of FLT3 in human hematologic malignancies", Blood, Apr. 15, 2021, vol. 97, No. 8, pp. 2434-2439.

Zhu, Zuoquan , et al., "FMS-Related Tyrosine Kinase 3 Ligand Promotes Radioresistance in Esophageal Squamous Cell Carcinoma", Frontiers in Pharmacology, May 2021, vol. 12, Article 659735, 11 pages.

* cited by examiner

[Figure 1a]
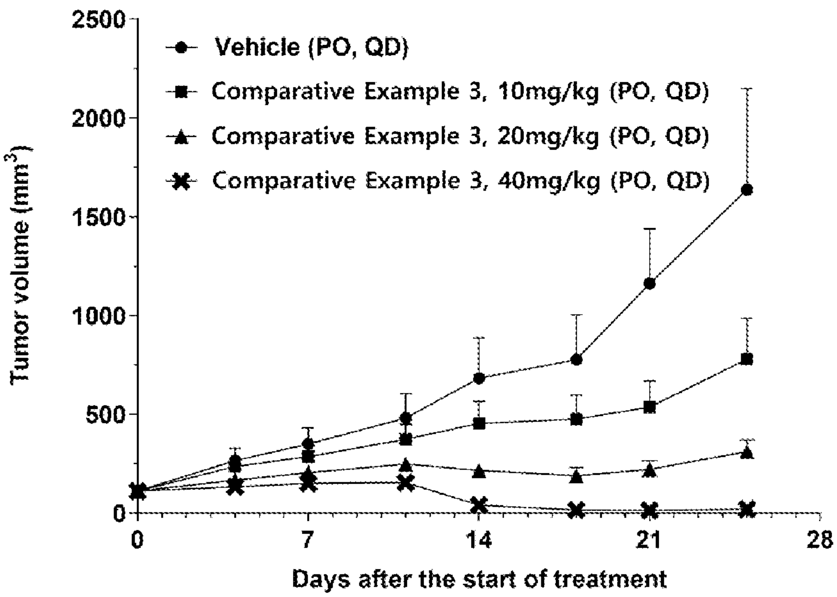
[Figure 1b]
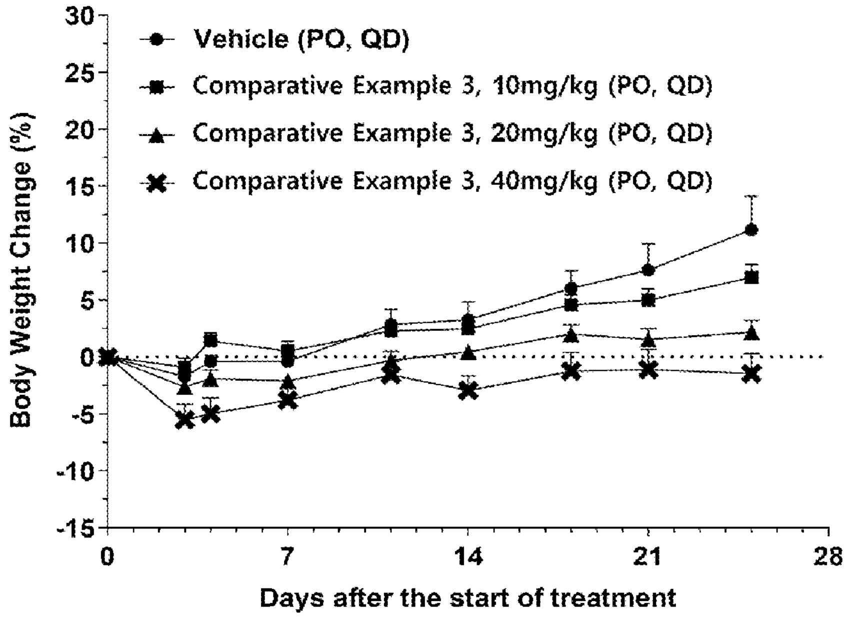

[Figure 1c]
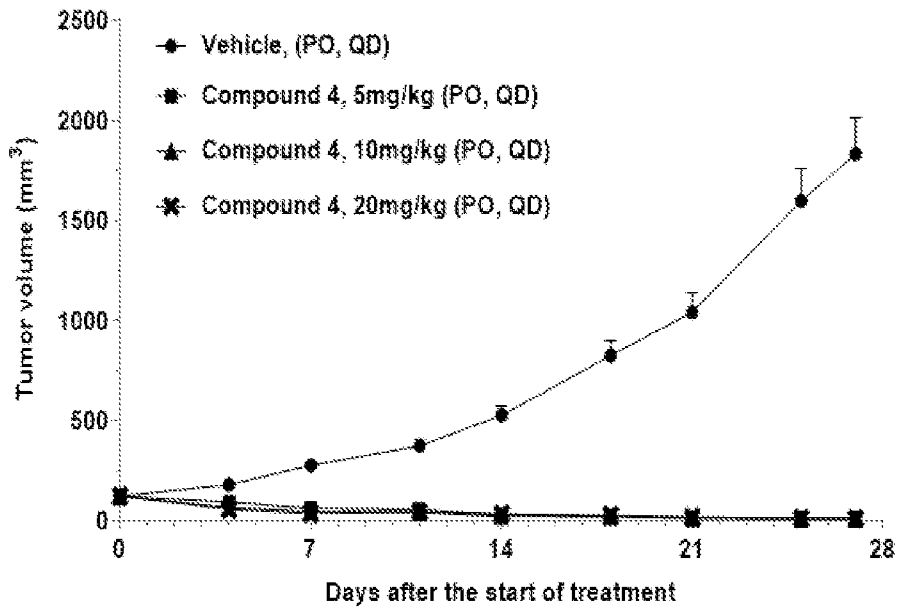
[Figure 1d]
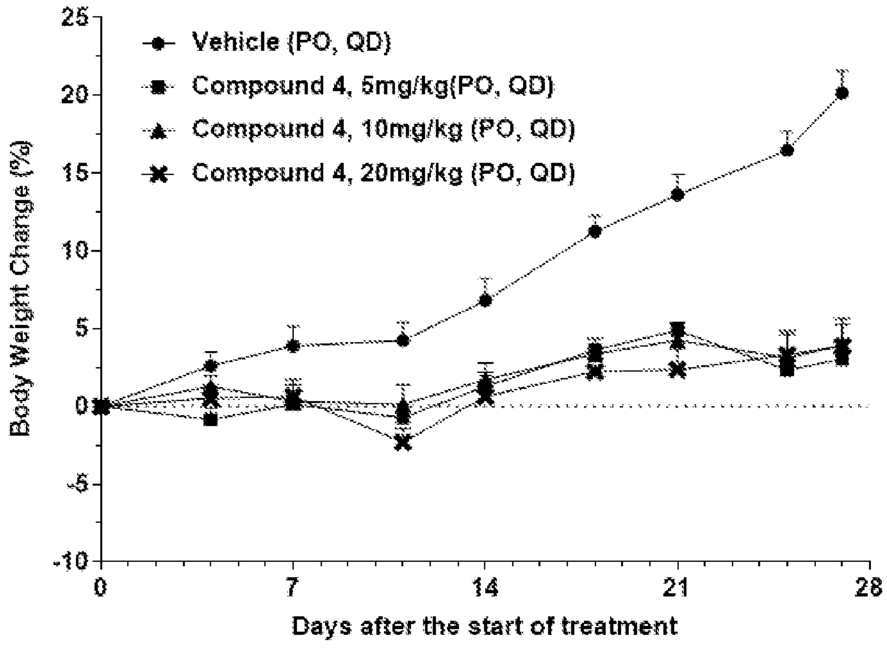

INDIRUBIN DERIVATIVES HAVING HETEROBICYCLIC MOIETIES AND THE USE THEREOF

CROSS-REFERENCE TO RELATED APPLICATIONS

This application is a National Phase entry of International Application No. PCT/KR2022/021194, filed Dec. 23, 2022, which claims priority to Korean Patent Application No. 10-2022-0019138, filed Feb. 14, 2022, the disclosures of which are incorporated herein by reference in their entireties.

FIELD OF THE INVENTION

The present invention relates to novel indirubin derivatives having heterobicyclic moieties, and use thereof as fms-like tyrosine kinase 3 (FLT3) inhibitors and rearranged during transfection (RET) kinase inhibitors.

BACKGROUND OF THE INVENTION

Fms-like tyrosine kinase 3 (FLT3) is a protein belonging to class III of receptor-type tyrosine kinases. FLT3 expression is confirmed on normal CD34-positive human bone marrow precursor cells and dendritic progenitor cells, and FLT plays an important role in proliferation and differentiation, etc. of these cells (Brown P et al., European Journal of Cancer, 40th, pp. 707-721, 2004). In addition, a ligand of FLT3 (FL) is expressed on bone marrow stromal cells and T cells, and affects the cell development of a number of hematopoietic lineage. Further, it is one of the cytokines which stimulates the proliferation of hepatocytes, precursor cells, dendritic cells and natural killer cells by the interaction with other growth factors.

It is known that FLT3 is a target antigen of acute myeloid leukemia (AML), is overexpressed in AML patients blasts when compared to healthy cells, and is expressed in the majority of patient cells (Carow et al., Feb. 2, 1996 Blood: 87 (3); Brig et al., November 1992 Blood: 80 (10)). In particular, FLT3 is a gene frequently mutated in AML patients, and such mutations are associated with poor prognosis (Abu-Duhier et al., British Journal of Haematology 2000 October; 111 (1): 190-5, Yamamoto et al., Apr. 15, 2001; Blood: 97 (8)). In addition, it has been recently reported that FLT3 may be an important biomarker related to the prognosis of pancreatic cancer (Ger et al., Anticancer Research 38:5759-5765 (2018)) and that the ligand of FLT 3 (FL) promotes the resistance of esophageal squamous cell carcinoma (Zhu et al., Frontiers in Pharmacology, May 2021, Vol 12, Article 659735). The relationship between FLT3 kinase and pancreatic cancer and esophageal cancer has also been confirmed.

A RET kinase is expressed during development in various tissues, including the peripheral nervous systems, central nervous systems and kidney, and is a single-pass transmembrane receptor belong to tyrosine kinases required for the development, maturation, and maintenance of several tissues and cell types (Mulligan, L. M., Nature Reviews Cancer, 2014, 14, 173-186). A RET protein consists of three domains of an extracellular ligand-binding domain, a hydrophobic transmembrane domain and a cytoplasmic part having a tyrosine kinase domain cleaved by insertions of 27 amino acids. Activating mutations in RET kinase have been found in patients with lung cancer and thyroid cancer, and are considered inducer mutations for these cancers (Kohno, T. et al., Nature Medicine, 2012, 18 (3), pp. 375-377, Matsubara, D. et al., Journal of Thoracic Oncology, 2012, 7 (12), pp. 1872-1876). In addition, the interdependence between RET-mediated autophagy inhibition and AML and the expression of RET kinase in MOLM-13 and MOLM-14, which are AML cell lines, have been reported (Rudat, et al., Leukemia 32, 2189-2202 (2018)). The relation between activating mutation of RET kinase and AML induction has been confirmed.

DISCLOSURE OF THE INVENTION

Problems to be Solved

As a result of the efforts to derive novel compounds having inhibitory activity against FLT3 and RET kinase, the inventors completed the present invention by identifying that novel indirubin derivatives having heterobicyclic moieties more effectively inhibit FLT3, particularly mutant FLT3, compared to previously known indirubin derivatives and excellent RET kinase inhibitory activity.

An object of the present invention is to provide the novel indirubin derivatives having heterobicyclic moieties, which have inhibitory activity against FLT3 and RET kinase, and a pharmaceutically acceptable salt thereof.

Another object of the present invention is to provide a pharmaceutical composition for preventing or treating FLT3 and RET kinase-related diseases, comprising the novel indirubin derivatives having heterobicyclic moieties. The present invention also provides an use of the novel compounds for preventing or treating FLT3 and RET kinase-related diseases, and a method for preventing or treating FLT3 and RET kinase-related diseases, comprising administering the novel compounds to a subject in need thereof.

Means for Solving the Problems

According to one embodiment of the present invention, a compound represented by the following formula (1) or a pharmaceutically acceptable salt thereof is provided.

[formula 1]

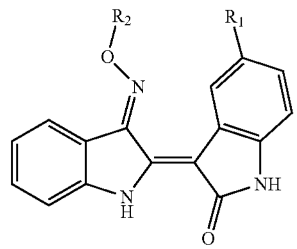

wherein, $R_1$ is hydrogen or halogen, and $R_2$ is

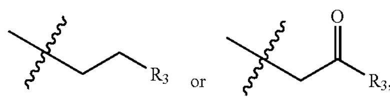

wherein $R_3$ is any one selected from the group consisting of

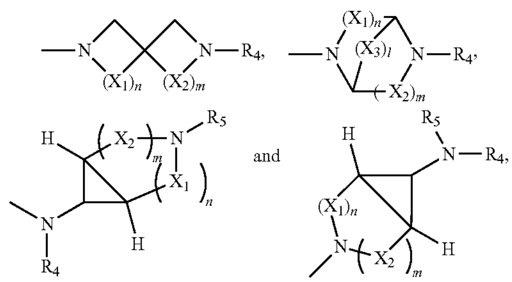

and wherein $X_1$ is C—$R_aR_b$, $X_2$ is C—$R_cR_a$, $X_3$ is C—$R_eR_f$, $R_4$, $R_5$, $R_a$, $R_b$, $R_c$, $R_a$, $R_e$ and $R_f$ are each independently hydrogen or $C_1$-$C_8$alkyl, and n, m and 1 are each independently an integer of 1 to 3.

The compounds disclosed herein have high inhibitory activity against FLT3 and RET kinases.

The compounds and pharmaceutical compositions disclosed herein are useful for preventing or treating FLT3-related diseases or RET kinase-related diseases, for example, by administering the compounds or compostions to a subject.

Advantage of the Invention

The indirubin derivative compound having a heterobicyclic moiety of the present invention is a novel compound that has not been previously known, and effectively inhibits the activities of FLT3 and RET kinase, and may be useful for preventing or treating of mutant FLT3 and mutant RET-related diseases, especially acute myeloid leukemia.

BRIEF DESCRIPTION OF DRAWINGS

FIGS. 1*a*-1*d* shows the changes in tumor size and body weight measured for a total of 28 days after the start of treatment in mice administered with an indirubin derivative compound having a heterobicyclic moiety of the present invention and a conventionally known indirubin derivative compound, respectively.

DETAILED DESCRIPTION OF THE INVENTION

Definition of Terms

Unless defined otherwise, all technical terms used herein have the same meaning as commonly understood by a person of ordinary skill in the art to which this invention belongs. Also, numerical values recited herein are intended to include the meaning of "about" unless explicitly stated otherwise.

Definitions of moieties and substituents as used herein are provided below. Unless otherwise specified, each moiety has the following definitions, and is used with the same meaning as commonly understood by those skilled in the art.

The substituents, as used herein, are intended to include both further substituted and unsubstituted instances.

As used herein, the terms "halo" or "halogen" refer to bromo, chloro, fluoro, or iodo. As used herein, the term "alkyl" is a hydrocarbon having primary, secondary, tertiary, and/or quaternary carbon atoms, including saturated aliphatic groups, which may be straight-chain, branched, cyclic, or combinations thereof. For example, an alkyl group may have 1 to 8 carbon atoms (i.e., C1-C8 alkyl), 1 to 6 carbon atoms (i.e., C1-C6 alkyl), or 1 to 3 carbon atoms (i.e., C1-C3 alkyl). Examples of suitable alkyl may include methyl (Me, —CH3), ethyl (Et,-C2H5), 1-propyl (n-Pr, —CH2CH2CH3), 2-propyl (i-Pr, —CH(CH3)2), 1-butyl (n-Bu,-CH2CH2CH2CH3), 2-methyl-1-propyl (i-Bu, —CH2CH(CH3)2), 2-butyl (s-Bu,-CH(CH3) CH2CH3), 2-methyl-2-propyl (t-Bu, —C(CH3)3), 1-pentyl (n-pentyl,-CH2CH2CH2CH2CH3), 2-pentyl (—CH(CH3) CH2CH2CH3), 3-pentyl (—CH(CH2$CH_3$)2), 2-methyl-2-butyl (—CH(CH3)2CH2CH3), 3-methyl-2-butyl (—CH (CH3) CH(CH3)2), 3-methyl-1-butyl (—CH2CH2CH (CH3)2), 2-methyl-1-butyl (—CH2CH(CH3) CH2CH3), 1-hexyl (—CH2CH2CH2CH2CH2CH3), 2-hexyl (—CH (CH3) CH2CH2CH2CH3), 3-hexyl (—CH(CH2$CH_3$) (CH2CH2CH3)), 2-methyl-2-pentyl (—C(CH3) 2CH2CH2CH3), 3-methyl-2-pentyl (—CH(CH3) CH(CH3) CH2CH3), 4-methyl-2-pentyl (—CH(CH3) CH2CH(CH3) 2), 3-methyl-3-pentyl (—C(CH3) (CH2$CH_3$)2), 2-methyl-3-pentyl (—CH(CH2$CH_3$) CH(CH3)2), 2,3-dimethyl-2-butyl (—C(CH3)2CH(CH3)2), 3,3-dimethyl-2-butyl (—CH (CH3)C(CH3)3), and octyl (—(CH2)7CH3), but is not limited thereto.

The phrase "pharmaceutically acceptable" is an expression used in the art to indicate that a substance or composition must be chemically and/or toxicologically compatible with the other components of the formulation and/or the mammal to be treated therewith.

"Pharmaceutically acceptable salt" or "salt" are used herein to refer to an acid or base addition salt suitable or compatible with the treatment of patients. An exemplary inorganic acid that forms a suitable salt may be hydrochloric acid, hydrobromic acid, sulfuric acid and phosphoric acid, as well as a metal salt, for example sodium monohydrogen orthophosphate and potassium hydrogen sulfate. An exemplary organic acid that forms a suitable salt may be mono-, di- and tricarboxylic acids, for example glycolic acid, lactic acid, pyruvic acid, malonic acid, succinic acid, glutaric acid, fumaric acid, malic acid, tartaric acid, citric acid, ascorbic acid, maleic acid, benzoic acid, phenylacetic acid, cinnamic acid and salicylic acid, as well as sulfonic acid, for example p-toluene sulfonic acid and methanesulfonic acid. Mono- or di-acid salts may be formed, and such salts may exist in hydrated, solvated or substantially anhydrous form. In general, acid addition salts of the compounds of the present invention are more soluble in water and various hydrophilic organic solvents compared to free base forms thereof, and generally exhibit higher melting points. The selection of suitable salts is known to those skilled in the art. Other non-pharmaceutically acceptable salts, for example, oxalates can be used in the isolation of the compounds of the present invention, for example for laboratory use or for subsequent conversion use as pharmaceutically acceptable acid addition salts. An exemplary inorganic base that forma a suitable salt may be lithium, sodium, potassium, calcium, magnesium, or barium hydroxides. An exemplary organic base that forma a suitable salt may be aliphatic, cycloaliphatic or aromatic organic amines, for example, methylamine, trimethylamine and picoline or ammonia. Thus, in some instances, contemplated salts of the present invention may be alkyl, dialkyl, trialkyl or tetra-alkyl ammonium salts. In certain embodiments, contemplated salts of the present invention may be L-arginine, benentamine, benzathine, betaine, calcium hydroxide, choline, theanol, diethanolamine, diethylamine, 2-(diethylamino) ethanol, Ethanolamine, ethylenediamine, N-methylglucamine, hydrabamine, 1H-imidazole, lithium, L-lysine, magnesium, 4-(2-hydroxyethyl) morpholine, piperazine, potassium, 1-(2-hydroxyethyl) pyrrolidine, sodium, triethanolamine, tromethamine, and zinc salts, but is not limited thereto. In certain embodiments, contemplated salts of the present invention may be, but is not limited thereto, Na, Ca, K, Mg, Zn or other metal salts.

The selection of appropriate salts is known to those skilled in the art.

Pharmaceutically acceptable acid addition salts may also exist as various solvates, for example, solvates with water, methanol, ethanol, dimethylformamide, and the like. Mixtures of these solvates can also be prepared. The source of such solvates may be from a solvent of crystallization, unique to a solvent of manufacture or crystallization, or accidental to such a solvent.

As used herein, the term "$IC_{50}$" refers to the concentration of an inhibitor or compound that produces 50% inhibition.

As used herein, the term "$GI_{50}$" refers to the concentration of an inhibitor or compound that produces 50% inhibition of maximal inhibition of cell proliferation.

As used herein, the terms "subject" and "patient" refer to a warm-blooded animal, for example, pig, cow, chicken, horse, guinea pig, mouse, rat, gerbil, cat, rabbit, dog, monkey, chimpanzees and humans.

As used herein, the terms "treat", "treating", "treatment" as well as "improvement" and "improving" refer to any objective or subjective parameter, e.g., decline; remission; reducing symptoms or making the symptom, injury, pathology or condition more tolerable by a patient; reduce the frequency or duration of a symptom or condition; in some circumstances, any indication of success in treating or ameliorating an injury, pathology, condition, or symptom (e.g., pain), including preventing the onset of the symptom or condition. Treatment or improvement of symptoms may be based on any objective or subjective parameter, for example, the results of a physical examination.

Heterobicyclic Indirubin Derivatives

The present invention provides novel heterobicyclic indirubin derivative compounds.

In one embodiment, the present invention relates to a heterobicyclic indirubin compound or a pharmaceutically acceptable salt thereof represented by Formula 1 below.

[Formula 1]

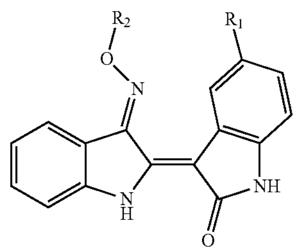

wherein, $R_1$ is hydrogen or halogen; and $R_2$ is

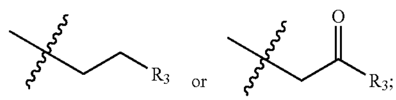

wherein $R_3$ is any one selected from the group consisting of

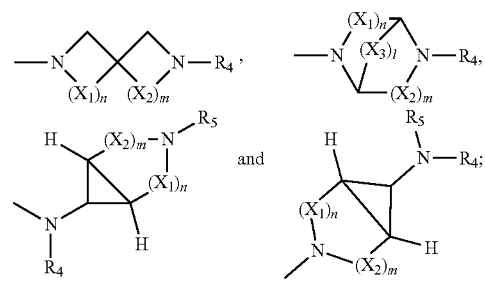

wherein $X_1$ is C—$R_aR_b$, $X_2$ is C—$R_cR_a$, $X_3$ is C—$R_eR_f$, $R_4$, $R_5$, $R_a$, $R_b$, $R_c$, $R_a$, $R_e$ and $R_f$ are each independently hydrogen or $C_1$-$C_8$alkyl, and n, m and 1 are each independently an integer of 1 to 3.

In one specific embodiment of the present invention, wherein $R_4$, $R_5$, $R_a$, $R_b$, $R_c$, Rd, $R_e$ and $R_f$ are each independently hydrogen or C1-C3 alkyl, and n, m and 1 are 1.

In one specific embodiment of the present invention, wherein $R_3$ is any one selected from the group consisting of

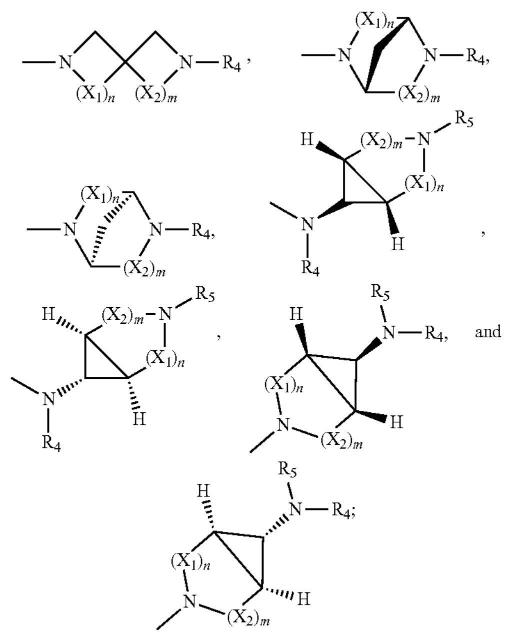

wherein n and m are each independently an integer of 1 to 3.

In one specific embodiment of the present invention, wherein $R_4$, $R_5$, $R_a$, $R_b$, $R_c$, and $R_a$ are each independently hydrogen or C1-C3 alkyl, and n and m are 1.

In one specific embodiment of the present invention, wherein $R_1$ is hydrogen or halogen, and $R_2$ is any one selected from the group consisting of

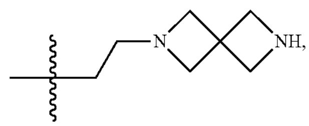

-continued

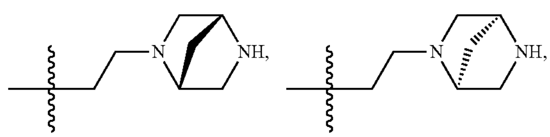

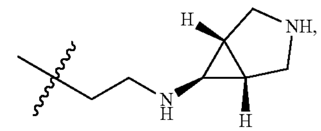

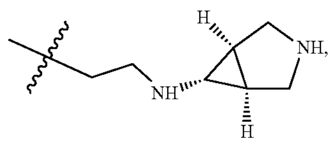

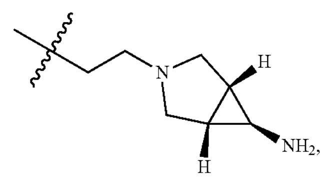

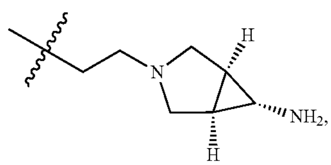

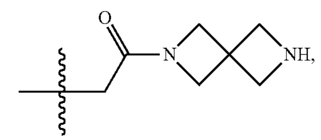

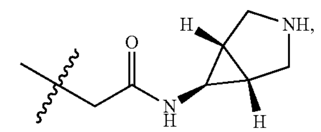

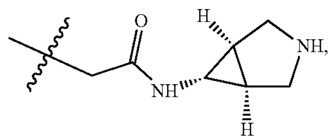

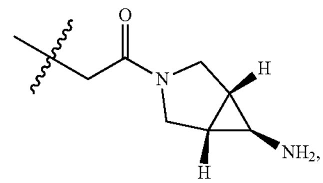

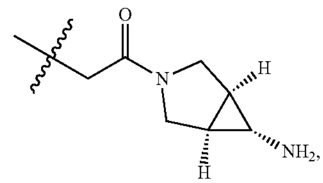

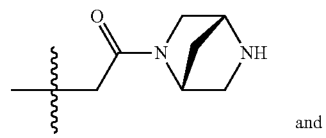

and

-continued

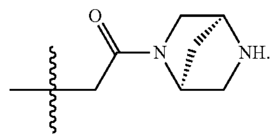

In one specific embodiment of the present invention, wherein $R_1$ is hydrogen or halogen, and $R_2$ is any one selected from the group consisting of

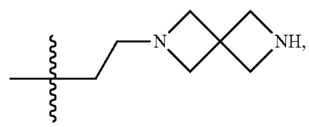

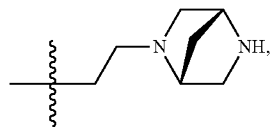

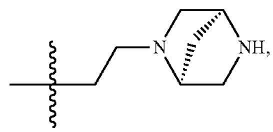

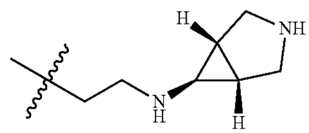

and

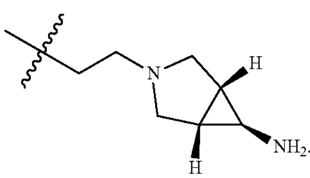

In one specific embodiment of the present invention, wherein $R_1$ is hydrogen or fluorine, and wherein $R_2$ is any one selected from the group consisting of

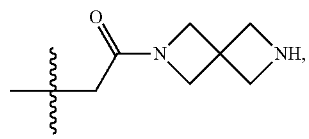

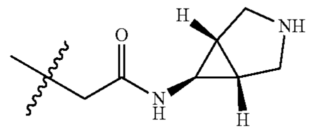

and

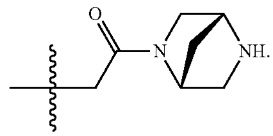

Representative compounds of the Formula 1 include, but are not limited to, compounds selected from the group consisting of compounds 1 to 20 below.

| COMPOUND | STRUCTURE | NAME |
|---|---|---|
| 1 | 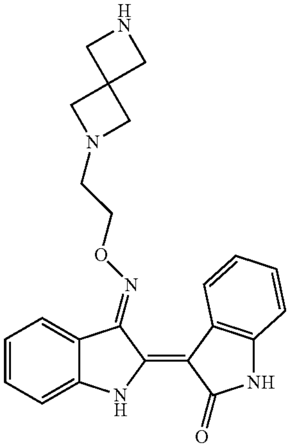 [SMILES: O=C1Nc2ccccc2/C1=C1/Nc2ccccc2/C1=N\OCCN1CC2(CNC2)C1] | (2Z,3E)-3-((2-(2,6-diazaspiro[3.3]heptane-2-yl)ethoxy)imino)-[2,3'-biindolinylidene]-2'-on |
| 2 | 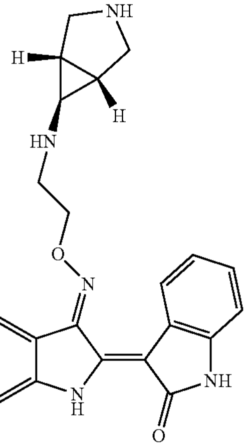 | (2Z,3E)-3-((2-((1R,5S,6s)-3-azabicyclo[3.1.0]hexane-6-ylamino)ethoxy)imino)-[2,3'-biindolinylidene]-2'-on |
| 3 | 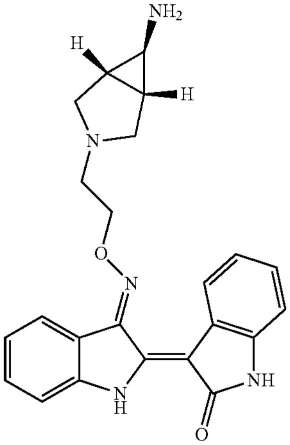 [SMILES: N[C@@H]1[C@H]2CN(CCO/N=C3/C(=C4/C(=O)Nc5ccccc54)Nc4ccccc43)C[C@@H]12] | (2Z,3E)-3-((2-((1R,5S,6s)-6-amino-3-azabicyclo[3.1.0]hexane-3-yl)ethoxy)imino)-[2,3'-biindolinylidene]-2'-on |

-continued

| COMPOUND | STRUCTURE | NAME |
|---|---|---|
| 4 | 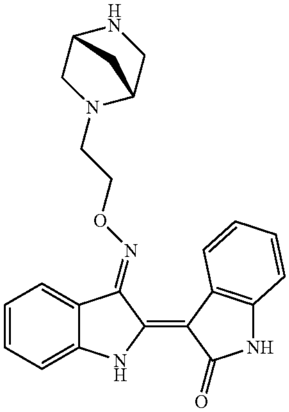 [SMILES: O=C1Nc2ccccc2/C1=C1/Nc2ccccc2/C1=N\OCCN1C[C@H]2C[C@@H]1CN2] | (2Z,3E)-3-((2-((1R,4R)-2,5-diazabicyclo[2.2.1]heptane-2-yl)ethoxy)imino)-[2,3'-biindolinylidene]-2'-on |
| 5 | 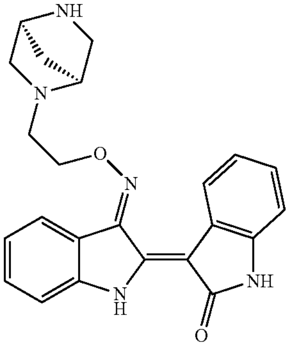 [SMILES: O=C1Nc2ccccc2/C1=C1/Nc2ccccc2/C1=N\OCCN1C[C@@H]2C[C@H]1CN2] | (2Z,3E)-3-((2-((1S,4S)-2,5-diazabicyclo[2.2.1]heptane-2-yl)ethoxy)imino)-[2,3'-biindolinylidene]-2'-on |
| 6 | 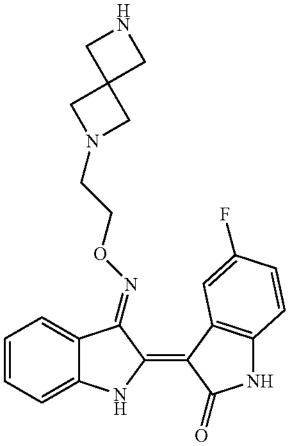 [SMILES: O=C1Nc2ccc(F)cc2/C1=C1/Nc2ccccc2/C1=N\OCCN1CC2(CNC2)C1] | (2Z,3E)-3-((2-(2,6-diazaspiro[3.3]heptane-2-yl)ethoxy)imino)-5'-fluoro-[2,3'-biindolinylidene]-2'-on |

-continued

| COMPOUND | STRUCTURE | NAME |
|---|---|---|
| 7 | 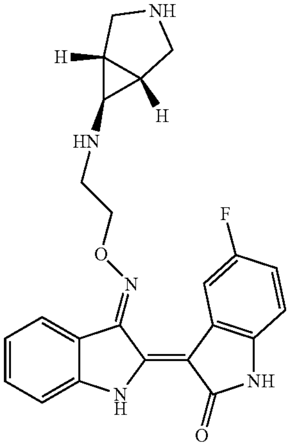 [SMILES: O=C1Nc2ccc(F)cc2/C1=C1/Nc2ccccc2/C1=N\OCCN[C@H]1[C@@H]2CNC[C@@H]21] | (2Z,3E)-3-((2-((1R,5S,6s)-3-azabicyclo[3.1.0]hexane-6-ylamino)ethoxy)imino)-5'-fluoro-[2,3'-biindolinylidene]-2'-on |
| 8 | 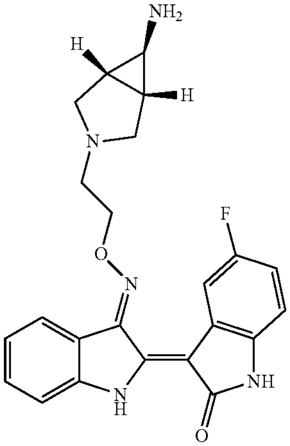 [SMILES: N[C@@H]1[C@H]2CN(CCO/N=C3/C(=C4/C(=O)Nc5ccc(F)cc54)Nc4ccccc43)C[C@@H]12] | (2Z,3E)-3-((2-((1R,5S,6s)-6-amino-3-azabicyclo[3.1.0]hexane-3-yl)ethoxy)imino)-5'-fluoro-[2,3'-biindolinylidene]-2'-on |
| 9 | 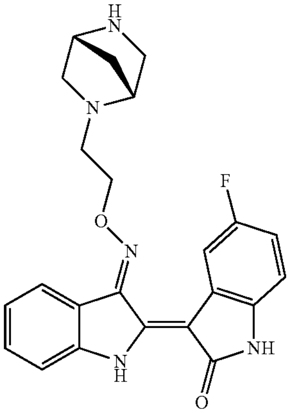 [SMILES: O=C1Nc2ccc(F)cc2/C1=C1/Nc2ccccc2/C1=N\OCCN1C[C@H]2C[C@@H]1CN2] | (2Z,3E)-3-((2-((1R,4R)-2,5-diazabicyclo[2.2.1]heptane-2-yl)ethoxy)imino)-5'-fluoro-[2,3'-biindolinylidene]-2'-on |

-continued

| COMPOUND | STRUCTURE | NAME |
|---|---|---|
| 10 | 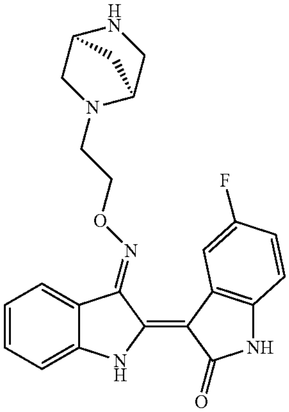 [SMILES: O=C1Nc2ccc(F)cc2/C1=C1/Nc2ccccc2/C1=N\OCCN1C[C@@H]2C[C@H]1CN2] | (2Z,3E)-3-((2-((1S,4S)-2,5-diazabicyclo[2.2.1]heptane-2-yl)ethoxy)imino)-5'-fluoro-[2,3'-biindolinylidene]-2'-on |
| 11 | 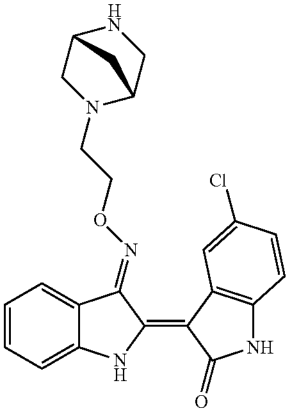 [SMILES: O=C1Nc2ccc(Cl)cc2/C1=C1/Nc2ccccc2/C1=N\OCCN1C[C@H]2C[C@@H]1CN2] | (2Z,3E)-3-((2-((1R,4R)-2,5-diazabicyclo[2.2.1]heptane-2-yl)ethoxy)imino)-5'-chloro-[2,3'-biindolinylidene]-2'-on |
| 12 | 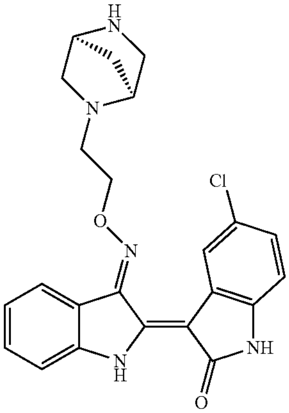 [SMILES: O=C1Nc2ccc(Cl)cc2/C1=C1/Nc2ccccc2/C1=N\OCCN1C[C@@H]2C[C@H]1CN2] | (1S,4S)-tert-butyl-5-(2-(((E)-((Z)-5'-chloro-2'-oxo-[2,3'-biindolinylidene]-3-ylidene)amino)oxy)ethyl)-2,5-diazabicyclo[2.2.1]heptane-2-carboxylate |

-continued

| COM-POUND | STRUCTURE | NAME |
|---|---|---|
| 13 | 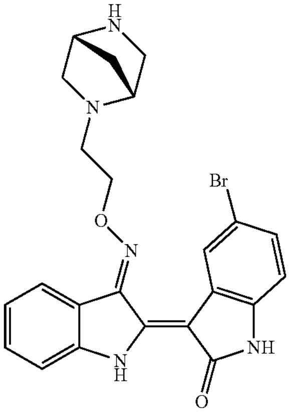 [SMILES: O=C1Nc2ccc(Br)cc2/C1=C1/Nc2ccccc2/C1=N\OCCN1C[C@H]2C[C@@H]1CN2] | (2Z,3E)-3-((2-((1R,4R)-2,5-diazabicyclo[2.2.1]heptane-2-yl)ethoxy)imino)-5'-bromo-[2,3'-biindolinylidene]-2'-on |
| 14 | 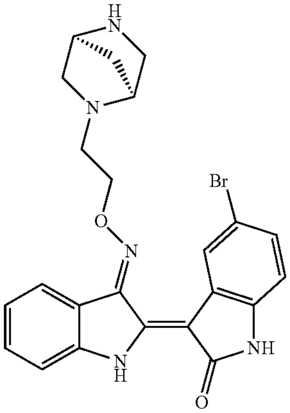 | (1S,4S)-tert-butyl-5-(2-(((E)-((Z)-5'-bromo-2'-oxo-[2,3'-biindolinylidene]-3-ylidene)amino)oxy)ethyl)-2,5-diazabicyclo[2.2.1]heptane-2-carboxylate |
| 15 | 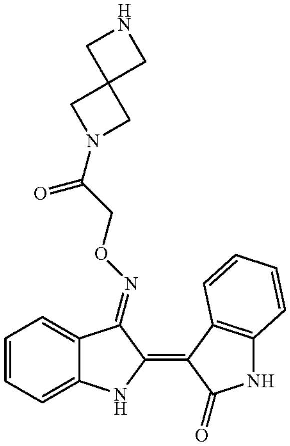 [SMILES: O=C1Nc2ccccc2/C1=C1/Nc2ccccc2/C1=N\OCC(=O)N1CC2(CNC2)C1] | (2Z,3E)-3-((2-oxo-2-(2,6-diazaspiro[3.3]heptane-2-yl)ethoxy)imino)-[2,3'-biindolinylidene]-2'-on |
| 16 | 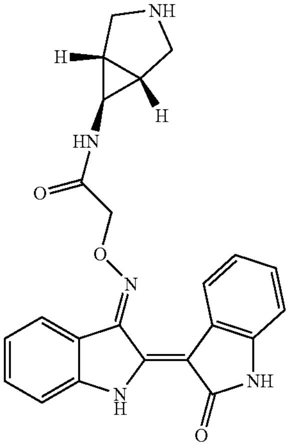 [SMILES: O=C(CO/N=C1/C(=C2/C(=O)Nc3ccccc32)Nc2ccccc21)N[C@H]1[C@@H]2CNC[C@@H]21] | N-((1R,5S,6s)-3-azabicyclo[3.1.0]hexane-6-yl)-2-(((E)-((Z)-2'-oxo-[2,3'-biindolinylidene]-3-ylidene)amino)oxy)acetamide |
| 17 | 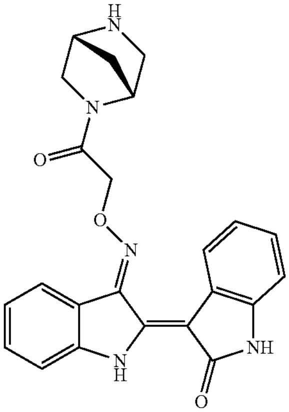 [SMILES: O=C1Nc2ccccc2/C1=C1/Nc2ccccc2/C1=N\OCC(=O)N1C[C@H]2C[C@@H]1CN2] | (2Z,3E)-3-((2-((1R,4R)-2,5-diazabicyclo[2.2.1]heptane-2-yl)-2-oxoethoxy)imino)-[2,3'-biindolinylidene]-2'-on |
| 18 | 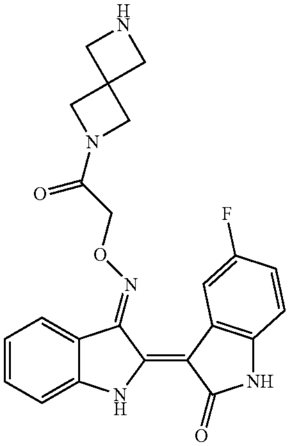 [SMILES: O=C1Nc2ccc(F)cc2/C1=C1/Nc2ccccc2/C1=N\OCC(=O)N1CC2(CNC2)C1] | (2Z,3E)-5'-fluoro-3-((2-oxo-2-(2,6-diazaspiro[3.3]heptane-2-yl)ethoxy)imino)-[2,3'-biindolinylidene]-2'-on |

-continued

| COMPOUND | STRUCTURE | NAME |
|---|---|---|
| 19 | 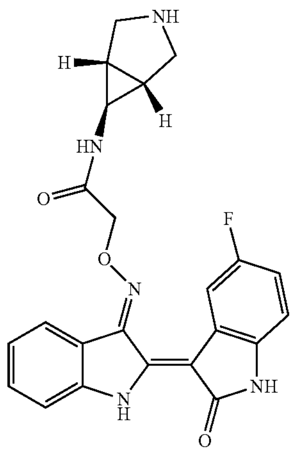 [SMILES: O=C(CO/N=C1/C(=C2/C(=O)Nc3ccc(F)cc32)Nc2ccccc21)N[C@H]1[C@@H]2CNC[C@@H]21] | N-((1R,5S,6s)-3-azabicyclo[3.1.0]hexane-6-yl)-2-(((E)-((Z)-5'-fluoro-2'-oxo-[2,3'-biindolinylidene]-3-ylidene)amino)oxy)acetamide |
| 20 | 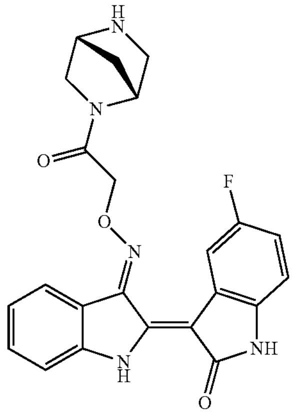 [SMILES: O=C1Nc2ccc(F)cc2/C1=C1/Nc2ccccc2/C1=N\OCC(=O)N1C[C@H]2C[C@@H]1CN2] | (2Z,3E)-3-((2-((1R,4R)-2,5-diazabicyclo[2.2.1]heptane-2-yl)-2-oxoethoxy)imino)-5'-fluoro-[2,3'-biindolinylidene]-2'-on |

In one specific embodiment of the present invention, the present invention relates to a pharmaceutical composition for preventing or treating FLT3 and RET-related diseases, comprising an indirubin derivative compound having a heterobicyclic moiety or a pharmaceutically acceptable salt thereof according to the present invention described above.

In one specific embodiment of the present invention, the pharmaceutical composition is for preventing or treating leukemia or lymphoma.

In one specific embodiment of the present invention, the pharmaceutical composition is for preventing or treating multiple myeloma, malignant plasma cell neoplasia, Hodgkin's lymphoma, nodular lymphocyte-predominant Hodgkin's lymphoma, Kahler's disease and myelomatosis, plasma cell leukemia, plasmacytoma, B-cell prolymphocytic leukemia, hairy-cell leukemia, B-Cell Non-Hodgkin's Lymphoma (NHL), Acute Myelogenous Leukemia (AML), Chronic Lymphocytic Leukemia (CLL), Acute Lymphocytic Leukemia (ALL), Chronic Myelogenous Leukemia (CML), Follicular lymphoma, Burkitt's lymphoma, marginal zone lymphoma, mantle cell lymphoma, large cell lymphoma, precursor B-lymphocytic lymphoma, myelogenous leukemia, Waldenstrom's macroglobulinemia, diffuse large B-cell lymphoma, follicular lymphoma, marginal zone lymphoma, mucosal-associated lymphoid tissue Lymphoma, small cell lymphocytic lymphoma, mantle cell lymphoma, Burkitt tumor, primary mediastinal (thymic) large B-cell lymphoma, lymphoplasmacytic lymphoma, Waldenstrom's macroglobulinemia, Lymphatic marginal zone B-cell lymphoma, splenic marginal zone lymphoma, intravascular giant B-Cell Lymphoma, Primary Exudative Lymphoma, Lymphomatous Granulomatosis, T cell/histiocyte-rich large B-cell lymphoma, primary central nervous system lymphoma, primary cutaneous diffuse large B-cell lymphoma (legged type), EBV-positive diffuse large B-cell lymphoma in the elderly, diffuse large B-cell lymphoma related with inflammation, intravascular large B-cell lymphoma, ALK-positive large B-cell lymphoma, plasmacytic lymphoma, large B-cell lymphoma arising from HHV8-associated multicentric Castleman's disease, unclassified B-cell lymphoma with intermediate features between diffuse large B-cell lymphoma and Burkitt's lymphoma, or unclassified B-cell lymphoma with intermediate features between diffuse large B-cell lymphoma and classical Hodgkin's lymphoma.

In one specific embodiment of the present invention, the pharmaceutical composition is for preventing or treating acute myeloid leukemia (AML).

In one specific embodiment of the present invention, the acute myeloid leukemia (AML) is the expression of mutant FLT3 or mutant RET kinase.

Therapeutic Use

The indirubin derivative compounds having novel heterobicyclic moieties or a pharmaceutically acceptable salt thereof according to the present invention inhibit the FLT3 or RET kinase, particularly the activity of mutant FLT3 and mutant RET kinase, and exhibit preventive or therapeutic effects on the diseases associated with these activities.

Mutant FLT3 may have a mutation in the tyrosine kinase domain (TKD) (FLT3-TKD) of the FLT3 amino acid sequence. The mutant FLT3 may further include internal tandem duplication (ITD). Examples of the mutant FLT3 include, but are not limited to, one or more of FLT3-ITD, FLT3-D835Y, FLT3-F691L, FLT3-F691L/D835Y, FLT3-ITD/D835Y, and FLT3-ITD/F691L.

Dysregulation of RET kinases expressions, activities or levels involves one or more point mutations/insertions/deletions of RET kinase proteins. Non-limiting examples of point mutations/insertions/deletions of RET kinase proteins include, but are not limited to, one or more of M918T, M918V, C634W, V840L, and V804M.

In one specific embodiment, the compounds of the present invention may be used to treat FLT3- and RET kinase related diseases. In some embodiments, the FLT3- and RET kinase related diseases include malignant cells expressing these kinases, for example, cancer. In some embodiments, the cancer includes cancer of hematopoietic origin, pancreatic cancer, esophageal cancer, lung cancer and thyroid cancer. In a specific embodiment, the cancer is cancer of hematopoietic origin, for example, lymphoma or leukemia. In a more specific embodiment, the cancer is multiple myeloma, malignant plasma cell neoplasia, Hodgkin's lymphoma, nodular lymphocyte-predominant Hodgkin's lymphoma, Kahler's disease and myelomatosis, plasma cell leukemia, plasmacytoma, B-cell prolymphocytic leukemia, hairy-cell leukemia, B-Cell Non-Hodgkin's Lymphoma (NHL), Acute Myelogenous Leukemia (AML), Chronic Lymphocytic Leukemia (CLL), Acute Lymphocytic Leukemia (ALL), Chronic Myelogenous Leukemia (CML), Follicular lymphoma, Burkitt's lymphoma, marginal zone lymphoma, mantle cell lymphoma, large cell lymphoma, precursor B-lymphocytic lymphoma, myelogenous leukemia, Waldenstrom's macroglobulinemia, diffuse large B-cell lymphoma, follicular lymphoma, marginal zone lymphoma, mucosal-associated lymphoid tissue Lymphoma, small cell lymphocytic lymphoma, mantle cell lymphoma, Burkitt tumor, primary mediastinal (thymic) large B-cell lymphoma, lymphoplasmacytic lymphoma, Waldenstrom's macroglobulinemia, Lymphatic marginal zone B-cell lymphoma, splenic marginal zone lymphoma, intravascular giant B-Cell Lymphoma, Primary Exudative Lymphoma, Lymphomatous Granulomatosis, T cell/histiocyte-rich large B-cell lymphoma, primary central nervous system lymphoma, primary cutaneous diffuse large B-cell lymphoma (legged type), EBV-positive diffuse large B-cell lymphoma in the elderly, diffuse large B-cell lymphoma related with inflammation, intravascular large B-cell lymphoma, ALK-positive large B-cell lymphoma, plasmacytic lymphoma, large B-cell lymphoma arising from HHV8-associated multicentric Castleman's disease, unclassified B-cell lymphoma with intermediate features between diffuse large B-cell lymphoma and Burkitt's lymphoma, or unclassified B-cell lymphoma with intermediate features between diffuse large B-cell lymphoma and classical Hodgkin's lymphoma, or other hematopoietic cell-related cancers, but not limited to. Preferably, the cancer is acute myeloid leukemia (AML), more preferably, AML in which mutant FLT3 or RET Kinase is Expressed.

The term, as used herein, "acute myeloid leukemia (AML)", is a cancer of the myeloid blood cell line, characterized by the rapid growth of abnormal blood cells derived from the bone marrow and interfering with normal blood cells. The main symptoms of AML are fatigue, rapid breathing, easy bruising and bleeding, and frequent infections. Although various factors presumed to be the cause of AML have been identified, the definite cause of AML have unknown. The compounds of the present invention, in particular, has the ability to inhibit mutant FLT3 and mutant RET kinases, and can be used as an AML therapeutic agent since the strong antiproliferative activity in MV4-11 cell line expressing FLT3-ITD, MOLM-13 cell line expressing FLT3-ITD and RET, MOLM14-FLT3/D835Y cell line expressing FLT3/D835Y and RET, etc. was confirmed.

Accordingly, the present invention provides a pharmaceutical composition for inhibiting FLT3 and RET kinase, comprising a compound or a pharmaceutically acceptable salt thereof according to the present invention as an active ingredient. In one embodiment, the pharmaceutical composition is for preventing or treating FLT3- and RET kinase-related diseases, more specifically, for preventing or treating AML.

In addition, the present invention provides a method for preventing or treating FLT-3 and RET kinase-related diseases, comprising administering a compound or a pharmaceutically acceptable salt thereof according to the present invention, or a pharmaceutical composition to a subject in need thereof.

In addition, the present invention provides a method of inhibiting FLT3 and RET kinase, comprising administering a pharmaceutically effective amount of a compound or a pharmaceutically acceptable salt thereof according to the present invention, or a pharmaceutical composition to a subject having AML diseases or a subject having a risk of onset of AML.

Additionally, the present invention provides a method for inhibiting FLT3, in which the pharmaceutical composition has strong antiproliferative activity in MV4-11 cell line expressing FLT3-ITD, MOLM-13 cell line expressing FLT3-ITD and RET, MOLM14-FLT3/D835Y cell line expressing FLT3/D835Y and RET.

In addition, the present invention provides the use of a compound or a pharmaceutically acceptable salt thereof according to the present invention for inhibiting FLT3 or preventing or treating FLT3-related diseases. The present invention also provides the use of a compound or a pharmaceutically acceptable salt thereof according to the present invention for the manufacture of a medicament for preventing or treating of AML.

In one specific embodiment, the indirubin derivative compound of the present invention may have an $IC_{50}$ value of 100 nM or less for FLT3 and RET kinase inhibition. More specifically, the compound represented by Formula 1 may have an $IC_{50}$ value of 50 nM or less, specifically 40 nM or less, more specifically 35 nM or less, even more specifically 30 nM or less, even more specifically 25 nM or less, even more specifically 20 nM or less, even more specifically 15 nM or less, and still even more specifically 10 nM or less for FLT3 and RET kinase inhibition.

Hereinafter, the present invention will be described in more detail through working examples. These examples are only for explaining the present invention in more detail, and it will be apparent to those skilled in the art that the scope of the present invention is not limited by these examples according to the gist of the present invention.

General Synthesis Methods

The compounds according to the present invention can be prepared from readily available starting materials using modifications to the specific synthetic protocols well known to those skilled in the art as described below.

According to procedure of schemes 1 and 2, indirubin analogues 6a-t (with ethyl linker), 8a-t (with ethenone linker), and substituents 10a-e were synthesized.

[Scheme 1] General synthesis pathway for preparation of indirubin derivative with bicyclic moieties

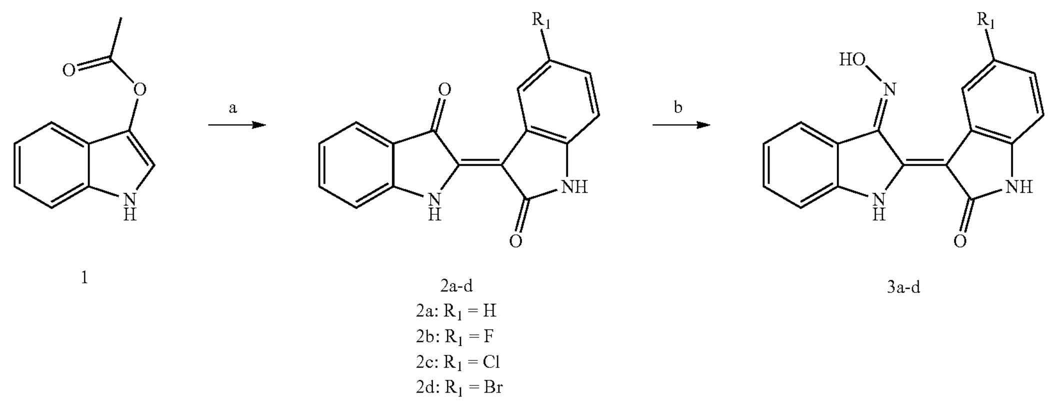

1

2a-d

2a: $R_1$ = H
2b: $R_1$ = F
2c: $R_1$ = Cl
2d: $R_1$ = Br 3a-d

-continued
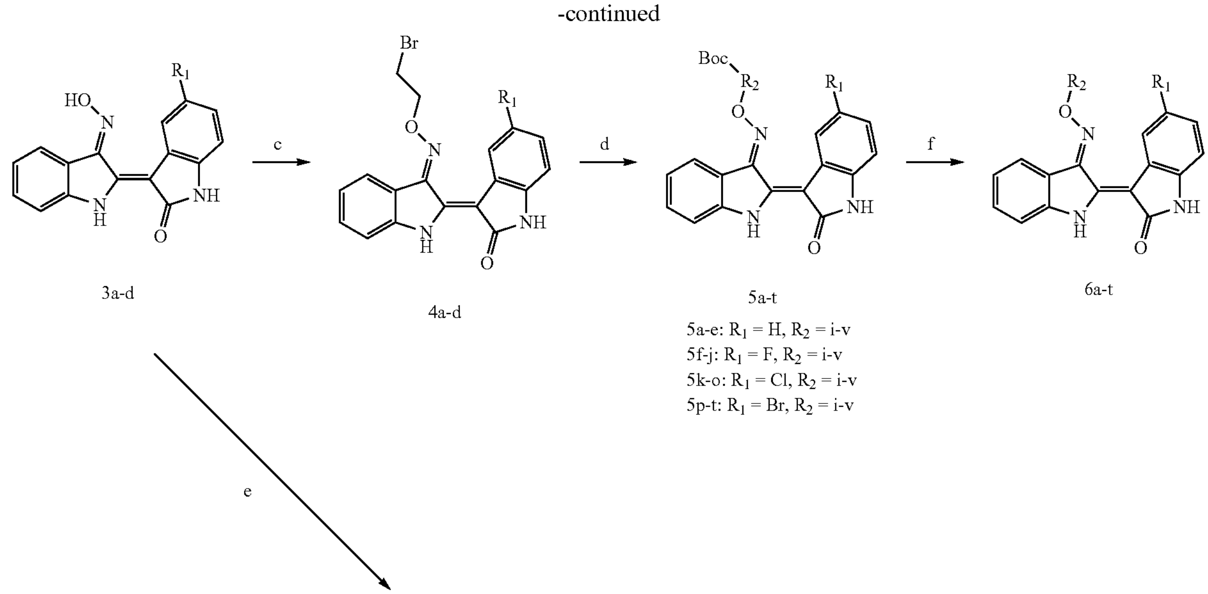
3a-d
4a-d
5a-t
5a-e: $R_1$ = H, $R_2$ = i-v
5f-j: $R_1$ = F, $R_2$ = i-v
5k-o: $R_1$ = Cl, $R_2$ = i-v
5p-t: $R_1$ = Br, $R_2$ = i-v
6a-t
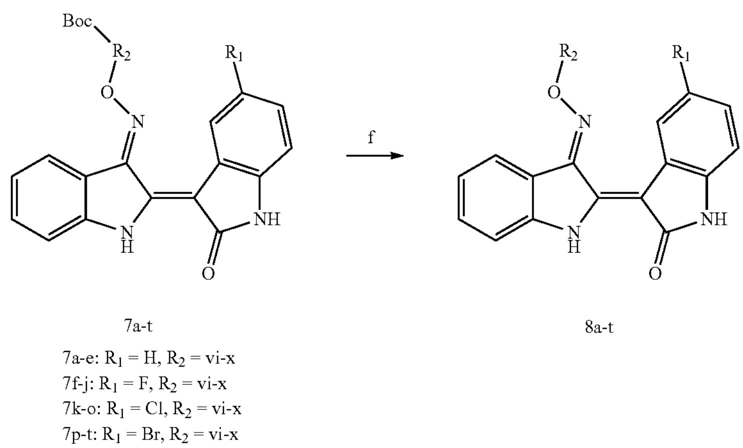
7a-t
7a-e: $R_1$ = H, $R_2$ = vi-x
7f-j: $R_1$ = F, $R_2$ = vi-x
7k-o: $R_1$ = Cl, $R_2$ = vi-x
7p-t: $R_1$ = Br, $R_2$ = vi-x
8a-t -continued $R_2$ =

(i) 2-ethyl-2,6-diazaspiro[3.3]heptane

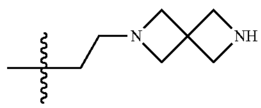

(ii) (1R,5S,6s)-N-ethyl-3-azabicyclo[3.1.0]hexan-6-amine

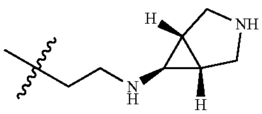

(iii) (1R,5S,6s)-3-ethyl-3-azabicyclo[3.1.0]hexan-6-amine

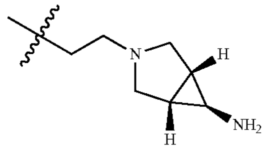

(iv) (1R,4R)-2-ethyl-2,5-diazabicyclo[2.2.1]heptane

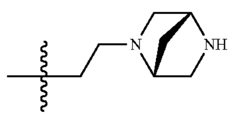

(v) (1S,4S)-2-ethyl-2,5-diazabicyclo[2.2.1]heptane

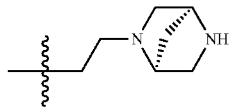

(vi) 1-(2,6-diazaspiro[3.3]heptan-2-yl)ethan-1-one

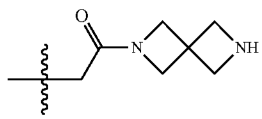

(vii) N-((1R,5S,6s)-3-azabicyclo[3.1.0]hexan-6-yl)acetamide

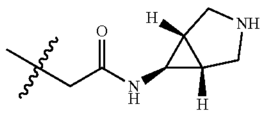

(viii) 1-((1R,5S,6s)-6-amino-3-azabicyclo[3.1.0]hexan-3-yl)ethan-1-one

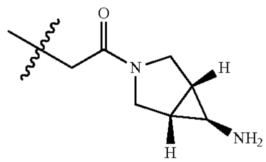

(ix) 1-((1R,4R)-2,5-diazabicyclo[2.2.1]heptan-2-yl)ethan-1-one

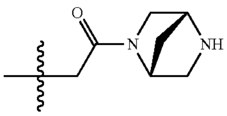

(x) 1-((1S,4S)-2,5-diazabicyclo[2.2.1]heptan-2-yl)ethan-1-one

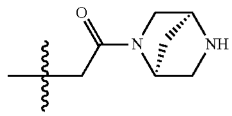

Reagents and Conditions:

(a) Various isatins, sodium methoxide, methanol, RT, 2 hrs, 63-65%;

(b) Hydroxylamine hydrochloride, KOH, sonication, 2 hrs, 89-91%;

(c) 1,2-dibromoethane, TEA, DMF, RT, overnight, 76-80%;

(d) Various boc-amines, DMF, 70° C., overnight, 85-87%;

(e) 10a-e, TEA, DMF, 70° C., 12 hrs, 80-84%;

(f) 20% TFA in DCM, 0° C., 2 hrs, 15-30%.

In Scheme 1, 5°-substituted indirubin derivatives 2a-d were prepared by conjugated reactions of compound 1, indoxyl acetate, with the various isatins under basic condition, and then 5-substituted-3-indirubin oxime derivatives 3-d were synthesized by the reaction of 2a-d with hydroxylamine to change from the ketone to N-oxime group. The compound 4a-d were obtained by nucleophilic substitution reactions between 1,2-dibromoethane and each N-oxime compound 3a-d. The compounds 5a-t were prepared by substitution of terminal bromides of 4a-d with various boc-protected amines containing bicyclic moieties under basic condition. After that, the final compound 6a-t having ethyl linker were prepared by deprotecting each boc group of 5a-t using 20% trifluoroacetic acid in dichloromethane. The compound 7a-t were prepared having ethanone linker between various indirubin N-oxime and boc-protected amine having bicyclic groups under the conditions similar with step d for the substitution of boc-protected heterocycles using compounds 3a-d and 10a-e. The final compounds 8a-t having ethanone linker were synthesized via corresponding boc-protected compounds 7a-t under the same condition described in step f.

The compounds 10a-e of various chloroacetamide reagents, were prepared from 2-chloroacetyl chloride and bicyclic moieties having five kinds of nitrogen under basic condition as shown in Scheme 2.

[Scheme 2] General synthesis pathway for preparation of 10a-e

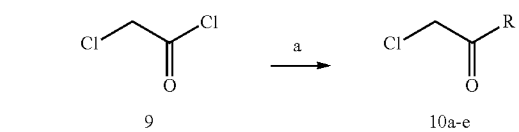

9 10a-e

10a: R = tert-butyl 2,6-diazaspiro[3.3]heptane-2-carboxylate

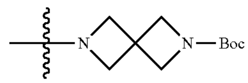

10b: R = (1R,5S,6s)-tert-butyl 6-amino-3-azabicyclo[3.1.0]hexane-3-carboxylate

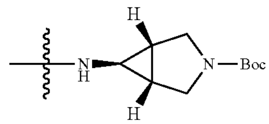

10c: R = tert-butyl ((1R,5S,6s)-3-azabicyclo[3.1.0]hexan-6-yl)carbamate

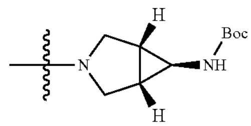

10d: R = (1R,4R)-tert-butyl 2,5-diazabicyclo[2.2.1]heptane-2-carboxylate

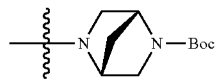

10e: R = (1S,4S)-tert-butyl 2,5-diazabicyclo[2.2.1]heptane-2-carboxylate

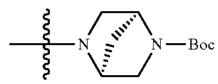

Reagents and conditions: (a) various boc-amines, TEA, DMF, 0° C., 2 hrs, 88-90%.

Synthesis Methods

All chemicals and solvents were obtained from chemical suppliers without purification. Column chromatography was carried out for purification using precoated silica gel plates (MERCK silica gel 60; F254, 0.040-0.063 mm). NMR spectra were obtained using JEOL ECS 400 NMR spectrometer (Tokyo, Japan) at 400 MHz of 1H frequency. Proton chemical shifts were measured in parts per million (ppm) relative to an internal standard. Chemical shifts, multiplicities, and coupling constants (J) were recorded and calculated using ACD NMR processor academic edition software. All synthesized compounds were analyzed using Waters ACQUITY ultra-performance liquid chromatograph (UPLC) coupled to a triple quadrupole mass spectrometer (Micromass Quattro Micro, Waters). Chromatographic separation was performed on a BEH C18 1.7 μm, 2.1 mm×50 mm column (Waters) maintained at 40° C. during separation under isocratic condition (Mobile phase A: Mobile phase B=20:80). Mobile phase A consisted of water (LC-MS grade) with 0.1% formic acid (v/v), and mobile phase B consisted of acetonitrile (LC-MS grade) with 0.1% formic acid (v/v). The flow rate was 0.2 ml/min.

Synthesis of (Z)-[2,3'-biindolinylidene]-2',3-dione (2a)

Isatin (1.3 eq) was added to a solution of indoxyl acetate, compound 1 (1 eq) in methanol (0.05 M). The reaction mixture was stirred at room temperature for 5 min. Then, Sodium methoxide powder (2 eq) was poured into reaction mixture and stirred for 2 hrs. TLC (chloroform:methanol=20:1, compound 1 Rf=0.9, product Rf=0.7) showed that indoxyl acetate was consumed completely and one new spot was detected. Afterwards, the reaction mixture was diluted with cold water to obtain precipitate of violet-colored product. The solid was filtered, and washed with water/methanol=2/1 solution and hexane. The solid was dried under reduced pressure at 40° C. for 5 hrs to obtain compound 2 with good purity.

Synthesis of (Z)-5'-fluoro-[2,3'-biindolinylidene]-2',3-dione (2b)

Compound 2b was synthesized from compound 1 and 5-fluoroisatin following the procedure described for compound 2a.

Synthesis of (Z)-5'-chloro-[2,3'-biindolinylidene]-2',3-dione (2c)

Compound 2c was synthesized from compound 1 and 5-chloroisatin following the procedure described for compound 2a.

Synthesis of (Z)-5'-bromo-[2,3'-biindolinylidene]-2',3-dione (2d)

Compound 2d was synthesized from compound 1 and 5-bromoisatin following the procedure described for compound 2a.

Synthesis of (2Z,3E)-3-(hydroxyimino)-[2,3'-biindolinylidene]-2'-one (3a)

12 equivalents of KOH solid was poured into reaction mixture and reaction vessel was sonicated for 30 min at 30° C. After completion of the reaction monitored by TLC, TLC (chloroform:methanol=20:1, compound 2a Rf=0.7, product Rf=0.6) showed that compound 2a was consumed completely and one new spot was detected. The reaction mixture was acidified with 1N HCl solution until pH 1~3 with concomitant precipitation of the red colored product. The solid was filtered, and washed with warm water and hexane. The solid was dried under reduced pressure at 40° C. for 4 hrs to obtain compound 3a.

Synthesis of (2Z,3E)-5'-fluoro-3-(hydroxyimino)-[2,3'-biindolinylidene]-2'-one (3b)

Compound 3b was synthesized from compound 2b following the procedure described for compound 3a.

Synthesis of (2Z,3E)-5'-chloro-3-(hydroxyimino)-[2,3'-biindolinylidene]-2'-one (3c)

Compound 3c was synthesized from compound 2c following the procedure described for compound 3a.

Synthesis of (2Z,3E)-5'-bromo-3-(hydroxyimino)-[2,3'-biindolinylidene]-2'-one (3d)

Compound 3d was synthesized from compound 2d following the procedure described for compound 3a.

Synthesis of (2Z,3E)-3-((2-bromoethoxy)imino)-[2,3'-biindolinylidene]-2'-one (4a)

TEA (7 eq) and 1,2-dibromoethane (7 eq) were added to a solution of compound 4 in DMF under argon atmosphere. The reaction mixture was stirred overnight at room temperature. After completion of the reaction monitored by TLC, TLC (chloroform:methanol=20:1, compound 3a Rf=0.6, product Rf=0.8) showed that compound 3a was consumed completely and one new spot was detected. The reaction mixture was diluted with cold water followed by the precipitation of the product. The precipitate was filtered, and washed with water and hexane. The solid was dried under reduced pressure at 40° C. for 4 hrs to obtain compound 4a.

Synthesis of (2Z,3E)-3-((2-bromoethoxy)imino)-5'-fluoro-[2,3'-biindolinylidene]-2'-one (4b)

Compound 4b was synthesized from compound 3b following the procedure described for compound 4a.

Synthesis of (2Z,3E)-3-((2-bromoethoxy)imino)-5'-chloro-[2,3'-biindolinylidene]-2'-one (4c)

Compound 4c was synthesized from compound 3c following the procedure described for compound 4a.

Synthesis of (2Z,3E)-5'-bromo-3-((2-bromoethoxy)imino)-[2,3'-biindolinylidene]-2'-one (4d)

Compound 4d was synthesized from compound 3d following the procedure described for compound 4a.

Synthesis of tert-butyl 6-(2-(((E)-((Z)-2'-oxo-[2,3'-biindolinylidene]-3-ylidene)amino)oxy)ethyl)-2,6-diazaspiro[3.3]heptane-2-carboxylate (5a)

4 equivalents of tert-butyl 2,6-diazaspiro[3.3]heptane-2-carboxylate and TEA (10 eq) were added to a solution of compound 4a in DMF under argon atmosphere. The reaction mixture was stirred at 70° C. for 12 hrs. After completion of the reaction monitored by TLC, TLC (chloroform:methanol=20:1, compound 4a Rf=0.8, product Rf=0.75) showed that compound 4a was consumed completely and one new spot was detected. Cold distilled water was poured into reaction mixture followed by the precipitation of the product. The solid was filtered, washed with water, and dried in vacuum oven at 60° C. for 5 hrs to obtain compound 5a.

Synthesis of (1R,5S,6s)-tert-butyl 6-((2-(((E)-((Z)-2'-oxo-[2,3'-biindolinylidene]-3-ylidene)amino)oxy)ethyl)amino)-3-azabicyclo[3.1.0]hexane-3-carboxylate (5b)

Compound 5b was synthesized from compound 4a and (1R,5S,6s)-tert-butyl 6-amino-3-azabicyclo[3.1.0]hexane-3-carboxylate following the procedure described for compound 5a.

Synthesis of tert-butyl ((1R,5S,6s)-3-(2-(((E)-((Z)-2'-oxo-[2,3'-biindolinylidene]-3-ylidene)amino)oxy)ethyl)-3-azabicyclo[3.1.0]hexan-6-yl) carbamate (5c)

Compound 5c was synthesized from compound 4a and tert-butyl ((1R,5S,6s)-3-azabicyclo[3.1.0]hexan-6-yl) carbamate following the procedure described for compound 5a.

Synthesis of (1R,4R)-tert-butyl 5-(2-(((E)-((Z)-2'-oxo-[2,3'-biindolinylidene]-3-ylidene)amino)oxy)ethyl)-2,5-diazabicyclo[2.2.1]heptane-2-carboxylate (5d)

Compound 5d was synthesized from compound 4a and tert-butyl (1R,4R)-2,5-diazabicyclo[2.2.1]heptane-2-carboxylate following the procedure described for compound 5a.

Synthesis of (1S,4S)-tert-butyl 5-(2-(((E)-((Z)-2'-oxo-[2,3'-biindolinylidene]-3-ylidene)amino)oxy)ethyl)-2,5-diazabicyclo[2.2.1]heptane-2-carboxylate (5e)

Compound 5e was synthesized from compound 4a and tert-butyl (1S,4S)-2,5-diazabicyclo[2.2.1]heptane-2-carboxylate following the procedure described for compound 5a.

Synthesis of tert-butyl 6-(2-(((E)-((Z)-5'-fluoro-2'-oxo-[2,3'-biindolinylidene]-3-ylidene)amino)oxy)ethyl)-2,6-diazaspiro[3.3]heptane-2-carboxylate (5f)

Compound 5f was synthesized from compound 4b and tert-butyl 2,6-diazaspiro[3.3]heptane-2-carboxylate following the procedure described for compound 5a.

Synthesis of (1R,5S,6s)-tert-butyl 6-((2-(((E)-((Z)-5'-fluoro-2'-oxo-[2,3'-biindolinylidene]-3-ylidene)amino)oxy)ethyl)amino)-3-azabicyclo[3.1.0]hexane-3-carboxylate (5g)

Compound 5g was synthesized from compound 4b and (1R,5S,6s)-tert-butyl 6-amino-3-azabicyclo[3.1.0]hexane-3-carboxylate following the procedure described for compound 5a.

Synthesis of tert-butyl ((1R,5S,6s)-3-(2-(((E)-((Z)-5'-fluoro-2'-oxo-[2,3'-biindolinylidene]-3-ylidene)amino)oxy)ethyl)-3-azabicyclo[3.1.0]hexan-6-yl)carbamate (5h)

Compound 5 h was synthesized from compound 4b and tert-butyl ((1R,5S,6s)-3-azabicyclo[3.1.0]hexan-6-yl) carbamate following the procedure described for compound 5a.

Synthesis of (1R,4R)-tert-butyl 5-(2-(((E)-((Z)-5'-fluoro-2'-oxo-[2,3'-biindolinylidene]-3-ylidene)amino)oxy)ethyl)-2,5-diazabicyclo[2.2.1]heptane-2-carboxylate (5i)

Compound 5i was synthesized from compound 4b and tert-butyl (1R,4R)-2,5-diazabicyclo[2.2.1]heptane-2-carboxylate following the procedure described for compound 5a.

Synthesis of (1S,4S)-tert-butyl 5-(2-(((E)-((Z)-5'-fluoro-2'-oxo-[2,3'-biindolinylidene]-3-ylidene)amino)oxy)ethyl)-2,5-diazabicyclo[2.2.1]heptane-2-carboxylate (5j)

Compound 5j was synthesized from compound 4b and tert-butyl (1S,4S)-2,5-diazabicyclo[2.2.1]heptane-2-carboxylate following the procedure described for compound 5a.

Synthesis of tert-butyl 6-(2-(((E)-((Z)-5'-chloro-2'-oxo-[2,3'-biindolinylidene]-3-ylidene)amino)oxy)ethyl)-2,6-diazaspiro[3.3]heptane-2-carboxylate (5k)

Compound 5k was synthesized from compound 4c and tert-butyl 2,6-diazaspiro[3.3]heptane-2-carboxylate following the procedure described for compound 5a.

Synthesis of (1R,5S,6s)-tert-butyl 6-((2-(((E)-((Z)-5'-chloro-2'-oxo-[2,3'-biindolinylidene]-3-ylidene)amino)oxy)ethyl)amino)-3-azabicyclo[3.1.0]hexane-3-carboxylate (51)

Compound 51 was synthesized from compound 4c and (1R,5S,6s)-tert-butyl 6-amino-3-azabicyclo[3.1.0]hexane-3-carboxylate following the procedure described for compound 5a.

Synthesis of tert-butyl ((1R,5S,6s)-3-(2-(((E)-((Z)-5'-chloro-2'-oxo-[2,3'-biindolinylidene]-3-ylidene)amino)oxy)ethyl)-3-azabicyclo[3.1.0]hexan-6-yl)carbamate (5m)

Compound 5m was synthesized from compound 4c and tert-butyl ((1R,5S,6s)-3-azabicyclo[3.1.0]hexan-6-yl) carbamate following the procedure described for compound 5a.

Synthesis of (1R,4R)-tert-butyl 5-(2-(((E)-((Z)-5'-chloro-2'-oxo-[2,3'-biindolinylidene]-3-ylidene)amino)oxy)ethyl)-2,5-diazabicyclo[2.2.1]heptane-2-carboxylate (5n)

Compound 5n was synthesized from compound 4c and tert-butyl (1R,4R)-2,5-diazabicyclo[2.2.1]heptane-2-carboxylate following the procedure described for compound 5a.

Examples 12: Synthesis of 1-((2Z,3E)-3-((2-((1S,4S)-2,5-diazabicyclo[2.2.1]heptan-2-yl) ethoxy)imino) indolin-2-ylidene)-6-chloro-1,3-dihydro-2H-inden-2-one (50)

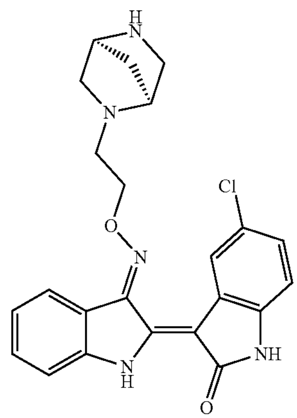

Compound 50 was synthesized from compound 4c and tert-butyl (1S,4S)-2,5-diazabicyclo[2.2.1]heptane-2-carboxylate following the procedure described for compound 5a.

$^1$H NMR (400 MHZ, DMSO-$d_6$) δ ppm 1.34-1.45 (m, 1H), 1.59-1.70 (m, 1H), 2.40-2.47 (m, 1H), 2.59-2.72 (m, 1H), 2.90-3.01 (m, 2H), 3.01-3.17 (m, 2H), 3.38-3.47 (m, 2H), 4.63 (t, J=5.84 Hz, 2H), 6.90 (d, J=8.24 Hz, 1H), 7.00-7.12 (m, 1H), 7.18 (dd, J=8.24, 2.29 Hz, 1H), 7.36-7.51 (m, 2H), 8.15 (dt, J=7.56, 0.92 Hz, 1H), 8.71 (d, J=2.06 Hz, 1H), 10.46-11.27 (m, 1H), 11.29-12.14 (m, 1H). MS (ESI): $[M+H]^+$=436.5.

Synthesis of tert-butyl 6-(2-(((E)-((Z)-5'-bromo-2'-oxo-[2,3'-biindolinylidene]-3-ylidene)amino)oxy)ethyl)-2,6-diazaspiro[3.3]heptane-2-carboxylate (5p)

Compound 5p was synthesized from compound 4d and tert-butyl 2,6-diazaspiro[3.3]heptane-2-carboxylate following the procedure described for compound 5a.

Synthesis of (1R,5S,6s)-tert-butyl 6-((2-(((E)-((Z)-5'-bromo-2'-oxo-[2,3'-biindolinylidene]-3-ylidene)amino)oxy)ethyl)amino)-3-azabicyclo[3.1.0]hexane-3-carboxylate (5q)

Compound 5q was synthesized from compound 4d and (1R,5S,6s)-tert-butyl 6-amino-3-azabicyclo[3.1.0]hexane-3-carboxylate following the procedure described for compound 5a.

Synthesis of tert-butyl ((1R,5S,6s)-3-(2-(((E)-((Z)-5'-bromo-2'-oxo-[2,3'-biindolinylidene]-3-ylidene)amino)oxy)ethyl)-3-azabicyclo[3.1.0]hexan-6-yl)carbamate (5r)

Compound 5r was synthesized from compound 4d and tert-butyl ((1R,5S,6s)-3-azabicyclo[3.1.0]hexan-6-yl) carbamate following the procedure described for compound 5a.

Synthesis of (1R,4R)-tert-butyl 5-(2-(((E)-((Z)-5'-bromo-2'-oxo-[2,3'-biindolinylidene]-3-ylidene) amino)oxy)ethyl)-2,5-diazabicyclo[2.2.1]heptane-2-carboxylate (5s)

Compound 5s was synthesized from compound 4d and tert-butyl (1R,4R)-2,5-diazabicyclo[2.2.1]heptane-2-carboxylate following the procedure described for compound 5a.

Examples 14: Synthesis of 1-((2Z,3E)-3-((2-((1S,4S)-2,5-diazabicyclo[2.2.1]heptan-2-yl) ethoxy) imino) indolin-2-ylidene)-6-bromo-1,3-dihydro-2H-inden-2-one (5t)

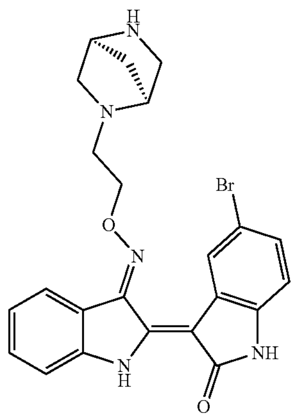 [SMILES: O=C1Nc2ccc(Br)cc2/C1=C1/Nc2ccccc2/C1=N\OCCN1C[C@@H]2C[C@H]1CN2]

Compound 5t was synthesized from compound 4d and tert-butyl (1S,4S)-2,5-diazabicyclo[2.2.1]heptane-2-carboxylate following the procedure described for compound 5a.

$^1$H NMR (400 MHz, DMSO-$d_6$) δ ppm 1.35-1.43 (m, 1H), 1.59-1.71 (m, 1H), 2.40-2.48 (m, 1H), 2.58-2.69 (m, 1H), 2.88-3.01 (m, 2H), 3.02-3.16 (m, 2H), 3.38-3.47 (m, 2H), 4.63 (td, J=6.01, 0.80 Hz, 2H), 6.86 (d, J=8.24 Hz, 1H), 6.98-7.14 (m, 1H), 7.27-7.35 (m, 1H), 7.40-7.52 (m, 2H), 8.15 (dt, J=7.79, 0.92 Hz, 1H), 8.86 (d, J=2.06 Hz, 1H), 10.54-11.26 (m, 1H), 11.36-12.11 (m, 1H). MS (ESI): $[M+H]^+$=480.4.

Examples 1: Synthesis of (2Z,3E)-3-((2-(2,6-diazaspiro[3.3]heptan-2-yl) ethoxy)imino)-[2,3'-biindolinylidene]-2'-one (6a)

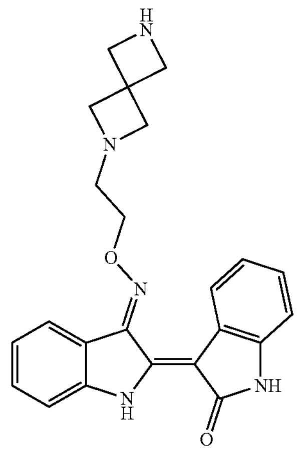 [SMILES: O=C1Nc2ccccc2/C1=C1/Nc2ccccc2/C1=N\OCCN1CC2(CNC2)C1]

20% TFA in DCM was slowly added to the solution of compound 5a in DCM for 2 hrs at 0° C. After completion of reaction by TLC monitoring, TLC (ammonia saturated chloroform:methanol=10:1, compound 5a Rf=0.9, product Rf=0.4) showed that compound 5a was completely consumed and one new spot was detected. After evaporation of solution, residue was suspended using minimum volume of methanol. The solution was slowly added to saturated aqueous $NaHCO_3$ solution for neutralization. The solid was filtered, washed with water and dried for 5 hrs at 60° C. in vacuum oven to obtain compound 6a. The mixture was purified by silica gel column chromatography (eluent: ammonia saturated chloroform:methanol=100:1).

$^1$H NMR (400 MHZ, DMSO-$d_6$) δ ppm 2.87 (t, J=5.61 Hz, 2H) 3.27 (s, 4H) 3.43 (s, 4H) 4.54 (t, J=5.61 Hz, 2H) 6.89-6.92 (m, 1H) 6.98 (td, J=7.67, 1.15 Hz, 1H) 7.02-7.07 (m, 1H) 7.13-7.18 (m, 1H) 7.40-7.47 (m, 2H) 8.14 (dt, J=7.67, 0.97 Hz, 1H) 8.61 (dd, J=7.90, 0.57 Hz, 1H) 10.79 (br. s., 1H). MS (ESI): $[M+H]^+$=401.7.

Example 2: Synthesis of (2Z,3E)-3-((2-((1R,5S,6s)-3-azabicyclo[3.1.0]hexan-6-ylamino) ethoxy)imino)-[2,3'-biindolinylidene]-2'-one (6b)

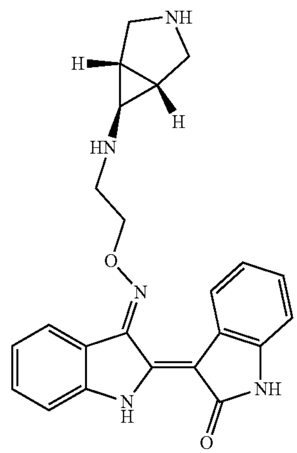 [SMILES: O=C1Nc2ccccc2/C1=C1/Nc2ccccc2/C1=N\OCCN[C@H]1[C@@H]2CNC[C@@H]21]

Compound 6b was synthesized from compound 5b following the procedure described for compound 6a.

$^1$H NMR (400 MHZ, DMSO-$d_6$) δ ppm 1.30 (s, 2H) 2.03 (t, J=1.95 Hz, 1H) 2.58 (s, 1H) 2.60 (s, 1H) 2.79 (s, 1H) 2.82 (s, 1H) 3.08 (t, J=5.84 Hz, 2H) 4.62 (t, J=5.72 Hz, 2H) 6.89-6.92 (m, 1H) 6.97-7.06 (m, 2H) 7.12-7.18 (m, 1H) 7.39-7.46 (m, 2H) 8.16 (dt, J=7.67, 0.97 Hz, 1H) 8.62 (d, J=8.01 Hz, 1H) 10.74-10.80 (m, 1H) 11.65-11.74 (m, 1H). MS (ESI): $[M+H]^+$=401.1.

Example 3: Synthesis of (2Z,3E)-3-((2-((1R,5S,6s)-6-amino-3-azabicyclo[3.1.0]hexan-3-yl) ethoxy) imino)-[2,3'-biindolinylidene]-2'-one (6c)

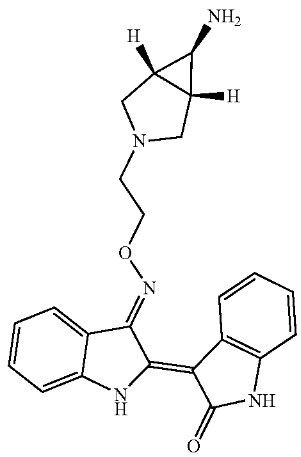

,

Compound 6c was synthesized from compound 5c following the procedure described for compound 6a.

$^1$H NMR (400 MHz, DMSO-$d_6$) δ ppm 1.15-1.28 (m, 2H), 1.49-1.79 (m, 2H), 2.36 (t, J=1.95 Hz, 1H), 2.40 (dt, J=8.47, 1.49 Hz, 2H), 2.90 (t, J=5.80 Hz, 2H), 3.04 (d, J=8.47 Hz, 2H), 4.61 (t, J=5.72 Hz, 2H), 6.86-6.93 (m, 1H), 6.98 (td, J=7.67, 1.15 Hz, 1H), 7.01-7.08 (m, 1H), 7.15 (td, J=7.60, 1.10 Hz, 1H), 7.37-7.49 (m, 2H), 8.15 (dt, J=7.67, 0.97 Hz, 1H), 8.60 (d, J=7.40 Hz, 1H), 10.63-10.91 (m, 1H), 11.31-12.03 (m, 1H). MS (ESI): $[M+H]^+$=402.5.

Example 4: Synthesis of (2Z,3E)-3-((2-((1R,4R)-2,5-diazabicyclo[2.2.1]heptan-2-yl) ethoxy)imino)-[2,3'-biindolinylidene]-2'-one (6d)

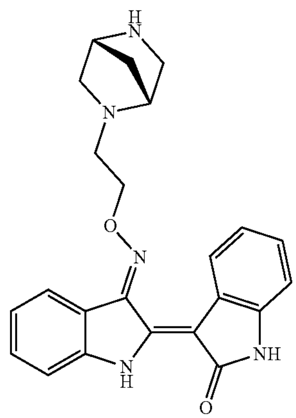

,

Compound 6d was synthesized from compound 5d following the procedure described for compound 6a.

$^1$H NMR (400 MHZ, DMSO-$d_6$) δ ppm 1.35-1.41 (m, 1H) 1.58-1.63 (m, 1H) 2.40 (d, J=8.70 Hz, 1H) 2.60 (dd, J=9.73, 1.03 Hz, 1H) 2.91-2.98 (m, 2H) 2.99-3.12 (m, 2H) 3.40 (br. s., 1H) 4.58-4.65 (m, 2H) 6.90 (d, J=7.79 Hz, 1H) 6.96-7.06 (m, 2H) 7.13-7.18 (m, 1H) 7.39-7.46 (m, 2H) 8.16 (dd, J=7.67, 0.57 Hz, 1H) 8.63 (d, J=7.79 Hz, 1H) 10.74-10.80 (m, 1H) 11.66-11.73 (m, 1H). MS (ESI): $[M+H]^+$=401.5.

Example 5: Synthesis of (2Z,3E)-3-((2-((1S,4S)-2,5-diazabicyclo[2.2.1]heptan-2-yl) ethoxy)imino)-[2,3'-biindolinylidene]-2'-one (6e)

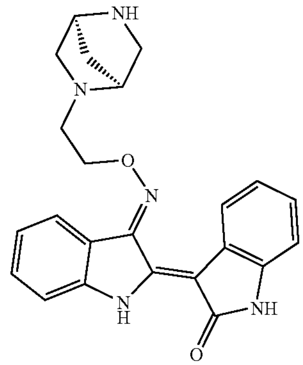 [SMILES: O=C1Nc2ccccc2/C1=C1/Nc2ccccc2/C1=N\OCCN1C[C@@H]2C[C@H]1CN2]

Compound 6e was synthesized from compound 5e following the procedure described for compound 6a.

$^1$H NMR (400 MHZ, DMSO-$d_6$) δ ppm 1.37-1.47 (m, 1H), 1.63-1.71 (m, 1H), 2.42-2.48 (m, 1H), 2.67 (dd, J=10.08, 2.29 Hz, 1H), 2.94 (dd, J=9.27, 2.40 Hz, 1H), 2.97-3.15 (m, 3H), 3.44-3.48 (m, 2H), 4.53-4.68 (m, 2H), 6.86-6.94 (m, 1H), 6.94-7.08 (m, 2H), 7.15 (td, J=7.61, 1.26 Hz, 1H), 7.33-7.50 (m, 2H), 8.10-8.20 (m, 1H), 8.63 (d, J=7.30 Hz, 1H), 10.66-10.90 (m, 1H), 11.69 (br. s., 1H). MS (ESI): $[M+H]^+$=402.5.

Example 6: Synthesis of (2Z,3E)-3-((2-(2,6-diazaspiro[3.3]heptan-2-yl) ethoxy)imino)-5'-fluoro-[2,3'-biindolinylidene]-2'-one (6f)

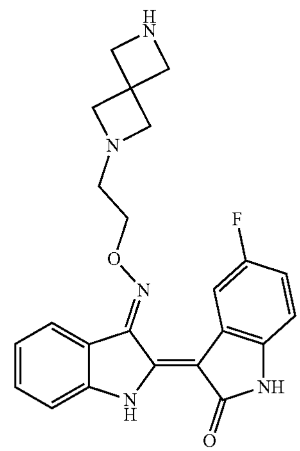 [SMILES: O=C1Nc2ccc(F)cc2/C1=C1/Nc2ccccc2/C1=N\OCCN1CC2(CNC2)C1]

Compound 6f was synthesized from compound 5f following the procedure described for compound 6a.

$^1$H NMR (400 MHZ, DMSO-$d_6$) δ ppm 2.89 (t, J=5.50 Hz, 2H) 3.27 (s, 2H) 3.29 (s, 4H) 3.43 (s, 2H) 4.54 (t, J=5.61 Hz, 2H) 6.84-6.90 (m, 1H) 6.95-7.02 (m, 1H) 7.07 (ddd, J=7.73, 5.21, 3.32 Hz, 1H) 7.42-7.50 (m, 2H) 8.15 (dt, J=7.56, 0.92 Hz, 1H) 8.45 (dd, J=11.33, 2.63 Hz, 1H) 10.74-10.86 (m, 1H). MS (ESI): $[M+H]^+$=420.2.

Example 7: Synthesis of (2Z,3E)-3-((2-((1R,5S,6s)-3-azabicyclo[3.1.0]hexan-6-ylamino) ethoxy)imino)-5'-fluoro-[2,3'-biindolinylidene]-2'-one (6g)

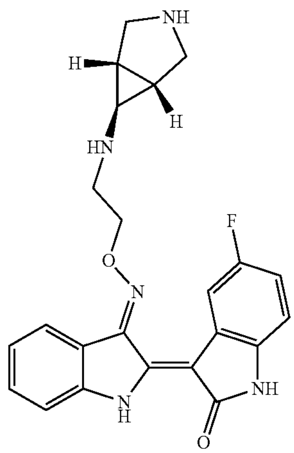 [SMILES: O=C1Nc2ccc(F)cc2/C1=C1/Nc2ccccc2/C1=N\OCCN[C@H]1[C@@H]2CNC[C@@H]21]

Compound 6g was synthesized from compound 5g following the procedure described for compound 6a.

$^1$H NMR (400 MHZ, DMSO-$d_6$) δ ppm 1.28-1.31 (m, 2H) 2.02 (t, J=1.95 Hz, 1H) 2.56-2.61 (m, 2H) 2.80 (d, J=10.99 Hz, 2H) 3.10 (t, J=5.84 Hz, 2H) 4.63 (t, J=5.84 Hz, 2H) 6.87 (dd, J=8.47, 5.04 Hz, 1H) 6.98 (td, J=8.82, 2.75 Hz, 1H) 7.06 (ddd, J=7.90, 5.15, 3.21 Hz, 1H) 7.42-7.48 (m, 2H) 8.16 (d, J=7.56 Hz, 1H) 8.45 (dd, J=11.33, 2.63 Hz, 1H) 10.78 (br. s., 1H). MS (ESI): $[M+H]^+$=420.3.

Example 8: Synthesis of (2Z,3E)-3-((2-((1R,5S,6s)-6-amino-3-azabicyclo[3.1.0]hexan-3-yl) ethoxy) imino)-5'-fluoro-[2,3'-biindolinylidene]-2'-one (6h)

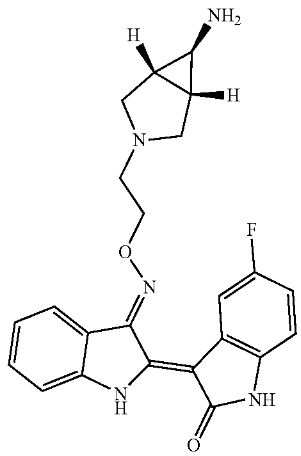

,

Compound 6 h was synthesized from compound 5 h following the procedure described for compound 6a.

$^1$H NMR (400 MHZ, DMSO-$d_6$) δ ppm 1.12-1.24 (m, 2H), 1.42-2.02 (m, 2H), 2.35 (t, J=1.95 Hz, 1H), 2.41 (dt, J=8.42, 1.52 Hz, 2H), 2.92 (t, J=6.00 Hz, 2H), 3.04 (d, J=8.50 Hz, 2H), 4.61 (t, J=6.00 Hz, 2H), 6.82-6.91 (m, 1H), 6.93-7.01 (m, 1H), 7.02-7.12 (m, 1H), 7.38-7.52 (m, 2H), 8.15 (dt, J=7.79, 0.92 Hz, 1H), 8.43 (dd, J=11.22, 2.52 Hz, 1H), 10.61-10.90 (m, 1H), 11.27-12.23 (m, 1H). MS (ESI): $[M+H]^+$=420.4.

Example 9: Synthesis of (2Z,3E)-3-((2-((1R,4R)-2,5-diazabicyclo[2.2.1]heptan-2-yl) ethoxy)imino)-5'-fluoro-[2,3'-biindolinylidene]-2'-one (6i)

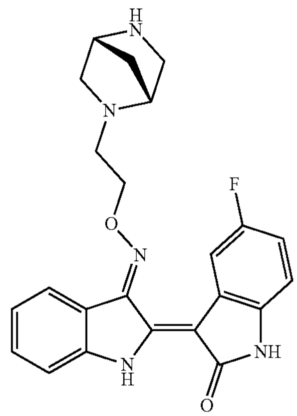

.

Compound 6i was synthesized from compound 5i following the procedure described for compound 6a.

$^1$H NMR (400 MHZ, DMSO-$d_6$) δ ppm 1.38 (d, J=8.01 Hz, 1H) 1.60 (d, J=8.70 Hz, 1H) 2.40 (d, J=9.85 Hz, 1H) 2.60 (dd, J=9.73, 2.18 Hz, 1H) 2.90-2.96 (m, 2H) 2.99-3.15 (m, 3H) 3.39 (s, 1H) 4.62 (t, J=5.84 Hz, 2H) 6.84-6.89 (m, 1H) 6.95-7.01 (m, 1H) 7.03-7.09 (m, 1H) 7.42-7.48 (m, 2H) 8.16 (dt, J=7.79, 0.92 Hz, 1H) 8.47 (dd, J=11.33, 2.63 Hz, 1H) 10.74-10.83 (m, 1H) 11.75 (br. s., 1H). MS (ESI): $[M+H]^+$=420.2.

Example 10: Synthesis of (2Z,3E)-3-((2-((1S,4S)-2,5-diazabicyclo[2.2.1]heptan-2-yl) ethoxy)imino)-5'-fluoro-[2,3'-biindolinylidene]-2'-one (6j)

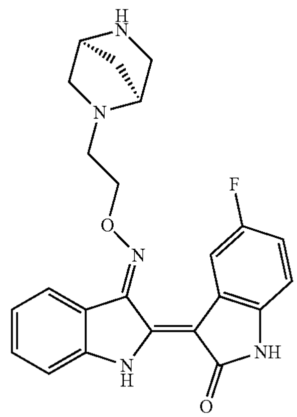

.

Compound 6j was synthesized from compound 5j following the procedure described for compound 6a.

$^1$H NMR (400 MHZ, DMSO-$d_6$) δ ppm 1.37-1.45 (m, 1H), 1.60-1.68 (m, 1H), 2.39-2.47 (m, 1H), 2.64 (dd, J=9.85, 2.06 Hz, 1H), 2.93 (dd, J=9.27, 2.40 Hz, 1H), 2.95-3.00 (m, 1H), 3.00-3.14 (m, 2H), 3.37-3.44 (m, 2H), 4.62 (t, J=6.40 Hz, 2H), 6.80-6.92 (m, 1H), 6.92-7.02 (m, 1H), 7.02-7.11 (m, 1H), 7.39-7.51 (m, 2H), 8.11-8.23 (m, 1H), 8.46 (dd, J=11.20, 2.80 Hz, 1H), 10.69-10.98 (m, 1H), 11.65-11.94 (m, 1H). MS (ESI): $[M+H]^+$=420.5.

Synthesis of (2Z,3E)-3-((2-(2,6-diazaspiro[3.3]heptan-2-yl) ethoxy)imino)-5'-chloro-[2,3'-biindolinylidene]-2'-one (6k)

Compound 6k was synthesized from compound 5k following the procedure described for compound 6a.

Synthesis of (2Z,3E)-3-((2-((1R,5S,6s)-3-azabicyclo[3.1.0]hexan-6-ylamino) ethoxy)imino)-5'-chloro-[2,3'-biindolinylidene]-2'-one (61)

Compound 61 was synthesized from compound 51 following the procedure described for compound 6a.

Synthesis of (2Z,3E)-3-((2-((1R,5S,6s)-6-amino-3-azabicyclo[3.1.0]hexan-3-yl) ethoxy)imino)-5'-chloro-[2,3'-biindolinylidene]-2'-one (6m)

Compound 6m was synthesized from compound 5m following the procedure described for compound 6a.

Example 11: Synthesis of (2Z,3E)-3-((2-((1R,4R)-2,5-diazabicyclo[2.2.1]heptan-2-yl) ethoxy)imino)-5'-chloro-[2,3'-biindolinylidene]-2'-one (6n)

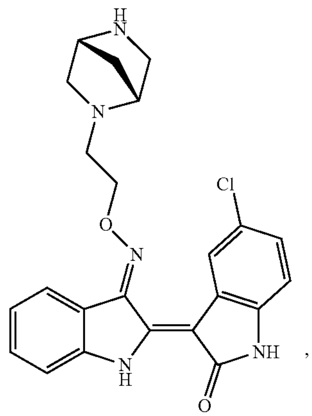 [SMILES: O=C1Nc2ccc(Cl)cc2/C1=C1/Nc2ccccc2/C1=N\OCCN1C[C@H]2C[C@@H]1CN2]

Compound 6n was synthesized from compound 5n following the procedure described for compound 6a.

$^1$H NMR (400 MHZ, DMSO-$d_6$) δ ppm 1.31-1.46 (m, 1H), 1.57-1.71 (m, 1H), 2.43 (d, J=9.80 Hz, 1H), 2.63 (dd, J=9.85, 2.29 Hz, 1H), 2.86-3.00 (m, 2H), 3.01-3.17 (m, 2H), 3.36-3.45 (m, 2H), 4.63 (t, J=6.20 Hz, 2H), 6.90 (d, J=8.24 Hz, 1H), 6.99-7.12 (m, 1H), 7.18 (dd, J=8.24, 2.29 Hz, 1H), 7.35-7.51 (m, 2H), 8.15 (dt, J=7.61, 1.00 Hz, 1H), 8.71 (d, J=2.06 Hz, 1H), 10.76-11.05 (m, 1H), 11.43-12.16 (m, 1H). MS (ESI): $[M+H]^+$=436.4.

Synthesis of (2Z,3E)-3-((2-((1S,4S)-2,5-diazabicyclo[2.2.1]heptan-2-yl) ethoxy)imino)-5'-chloro-[2,3'-biindolinylidene]-2'-one (60)

Compound 60 was synthesized from compound 50 following the procedure described for compound 6a.

Synthesis of (2Z,3E)-3-((2-(2,6-diazaspiro[3.3]heptan-2-yl) ethoxy)imino)-5'-bromo-[2,3'-biindolinylidene]-2'-one (6p)

Compound 6p was synthesized from compound 5p following the procedure described for compound 6a.

Synthesis of (2Z,3E)-3-((2-((1R,5S,6s)-3-azabicyclo[3.1.0]hexan-6-ylamino) ethoxy)imino)-5'-bromo-[2,3'-biindolinylidene]-2'-one (6q)

Compound 6q was synthesized from compound 5q following the procedure described for compound 6a.

Synthesis of (2Z,3E)-3-((2-((1R,5S,6s)-6-amino-3-azabicyclo[3.1.0]hexan-3-yl) ethoxy)imino)-5'-bromo-[2,3'-biindolinylidene]-2'-one (6r)

Compound 6r was synthesized from compound 5r following the procedure described for compound 6a.

Example 13: Synthesis of (2Z,3E)-3-((2-((1R,4R)-2,5-diazabicyclo[2.2.1]heptan-2-yl) ethoxy)imino)-5'-bromo-[2,3'-biindolinylidene]-2'-one (6s)

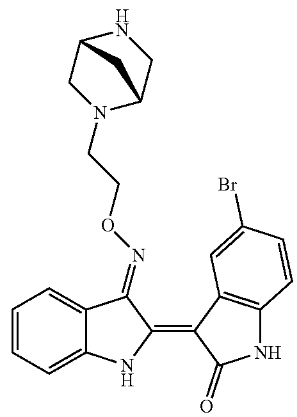 [SMILES: O=C1Nc2ccc(Br)cc2/C1=C1/Nc2ccccc2/C1=N\OCCN1C[C@H]2C[C@@H]1CN2]

Compound 6s was synthesized from compound 5s following the procedure described for compound 6a.

$^1$H NMR (400 MHz, DMSO-$d_6$) δ ppm 1.33-1.43 (m, 1H), 1.55-1.66 (m, 1H), 2.41 (dd, J=9.04, 1.03 Hz, 1H), 2.60 (dd, J=9.85, 2.29 Hz, 1H), 2.90-3.00 (m, 2H), 3.02-3.17 (m, 2H), 3.36-3.43 (m, 2H), 4.63 (td, J=6.01, 0.80 Hz, 2H), 6.86 (d, J=8.24 Hz, 1H), 7.02-7.11 (m, 1H), 7.30 (dd, J=8.20, 2.10 Hz, 1H), 7.41-7.50 (m, 2H), 8.15 (dt, J=7.61, 1.00 Hz, 1H), 8.86 (d, J=2.06 Hz, 1H), 10.60-11.27 (m, 1H), 11.34-12.09 (m, 1H). MS (ESI): $[M+H]^+$=482.3.

Synthesis of (2Z,3E)-3-((2-((1S,4S)-2,5-diazabicyclo[2.2.1]heptan-2-yl) ethoxy)imino)-5'-bromo-[2,3'-biindolinylidene]-2'-one (6t)

Compound 6t was synthesized from compound 5t following the procedure described for compound 6a.

Synthesis of tert-butyl 6-(2-(((E)-((Z)-2'-oxo-[2,3'-biindolinylidene]-3-ylidene)amino)oxy) acetyl)-2,6-diazaspiro[3.3]heptane-2-carboxylate (7a)

4 equivalents of compound 10a and TEA (10 eq) were added to a solution of compound 3a in DMF under argon atmosphere. The reaction mixture was stirred at 70° C. for 12 hrs. After completion of the reaction monitored by TLC, TLC (chloroform:methanol=20:1, compound 3a Rf=0.8, product Rf=0.75) showed that compound 3a was consumed completely and one new spot was detected. Cold distilled water was poured into reaction mixture followed by the precipitation of the product. The solid was filtered, washed with water, and dried in vacuum oven at 60° C. for 5 hrs to obtain compound 7a.

Synthesis of (1R,5S,6s)-tert-butyl 6-(2-(((E)-((Z)-2'-oxo-[2,3'-biindolinylidene]-3-ylidene)amino)oxy) acetamido)-3-azabicyclo[3.1.0]hexane-3-carboxylate (7b)

Compound 7b was synthesized from compounds 3a and 10b following the procedure described for compound 7a.

Synthesis of tert-butyl ((1R,5S,6s)-3-(2-(((E)-((Z)-2'-oxo-[2,3'-biindolinylidene]-3-ylidene)amino)oxy) acetyl)-3-azabicyclo[3.1.0]hexan-6-yl) carbamate (7c)

Compound 7c was synthesized from compounds 3a and 10c following the procedure described for compound 7a.

Synthesis of (1R,4R)-tert-butyl 5-(2-(((E)-((Z)-2'-oxo-[2,3'-biindolinylidene]-3-ylidene)amino)oxy) acetyl)-2,5-diazabicyclo[2.2.1]heptane-2-carboxylate (7d)

Compound 7d was synthesized from compounds 3a and 10d following the procedure described for compound 7a.

Synthesis of (1S,4S)-tert-butyl 5-(2-(((E)-((Z)-2'-oxo-[2,3'-biindolinylidene]-3-ylidene)amino)oxy) acetyl)-2,5-diazabicyclo[2.2.1]heptane-2-carboxylate (7e)

Compound 7e was synthesized from compounds 3a and 10e following the procedure described for compound 7a.

Synthesis of tert-butyl 6-(2-(((E)-((Z)-5'-fluoro-2'-oxo-[2,3'-biindolinylidene]-3-ylidene)amino)oxy) acetyl)-2,6-diazaspiro[3.3]heptane-2-carboxylate (7f)

Compound 7f was synthesized from compounds 3b and 10a following the procedure described for compound 7a.

Synthesis of (1R,5S,6s)-tert-butyl 6-(2-(((E)-((Z)-5'-fluoro-2'-oxo-[2,3'-biindolinylidene]-3-ylidene) amino)oxy) acetamido)-3-azabicyclo[3.1.0]hexane-3-carboxylate (7g)

Compound 7g was synthesized from compounds 3b and 10b following the procedure described for compound 7a.

Synthesis of tert-butyl ((1R,5S,6s)-3-(2-(((E)-((Z)-5'-fluoro-2'-oxo-[2,3'-biindolinylidene]-3-ylidene) amino)oxy) acetyl)-3-azabicyclo[3.1.0]hexan-6-yl) carbamate (7h)

Compound 7 h was synthesized from compounds 3b and 10c following the procedure described for compound 7a.

Synthesis of (1R,4R)-tert-butyl 5-(2-(((E)-((Z)-5'-fluoro-2'-oxo-[2,3'-biindolinylidene]-3-ylidene) amino)oxy) acetyl)-2,5-diazabicyclo[2.2.1]heptane-2-carboxylate (7i)

Compound 7i was synthesized from compounds 3b and 10d following the procedure described for compound 7a.

Synthesis of (1S,4S)-tert-butyl 5-(2-(((E)-((Z)-5'-fluoro-2'-oxo-[2,3'-biindolinylidene]-3-ylidene) amino)oxy) acetyl)-2,5-diazabicyclo[2.2.1]heptane-2-carboxylate (7j)

Compound 7j was synthesized from compounds 3b and 10e following the procedure described for compound 7a.

Synthesis of tert-butyl 6-(2-(((E)-((Z)-5'-chloro-2'-oxo-[2,3'-biindolinylidene]-3-ylidene)amino)oxy) acetyl)-2,6-diazaspiro[3.3]heptane-2-carboxylate (7k)

Compound 7k was synthesized from compounds 3c and 10a following the procedure described for compound 7a.

Synthesis of (1R,5S,6s)-tert-butyl 6-(2-(((E)-((Z)-5'-chloro-2'-oxo-[2,3'-biindolinylidene]-3-ylidene) amino)oxy) acetamido)-3-azabicyclo[3.1.0]hexane-3-carboxylate (71)

Compound 71 was synthesized from compounds 3c and 10b following the procedure described for compound 7a.

Synthesis of tert-butyl ((1R,5S,6s)-3-(2-(((E)-((Z)-5'-chloro-2'-oxo-[2,3'-biindolinylidene]-3-ylidene) amino)oxy) acetyl)-3-azabicyclo[3.1.0]hexan-6-yl) carbamate (7m)

Compound 7m was synthesized from compounds 3c and 10c following the procedure described for compound 7a.

Synthesis of (1R,4R)-tert-butyl 5-(2-(((E)-((Z)-5'-chloro-2'-oxo-[2,3'-biindolinylidene]-3-ylidene) amino)oxy) acetyl)-2,5-diazabicyclo[2.2.1]heptane-2-carboxylate (7n)

Compound 7n was synthesized from compounds 3c and 10d following the procedure described for compound 7a.

Synthesis of (1S,4S)-tert-butyl 5-(2-(((E)-((Z)-5'-chloro-2'-oxo-[2,3'-biindolinylidene]-3-ylidene) amino)oxy) acetyl)-2,5-diazabicyclo[2.2.1]heptane-2-carboxylate (7o)

Compound 70 was synthesized from compounds 3c and 10e following the procedure described for compound 7a.

Synthesis of tert-butyl 6-(2-(((E)-((Z)-5'-bromo-2'-oxo-[2,3'-biindolinylidene]-3-ylidene)amino)oxy) acetyl)-2,6-diazaspiro[3.3]heptane-2-carboxylate (7p)

Compound 7p was synthesized from compounds 3d and 10a following the procedure described for compound 7a.

Synthesis of (1R,5S,6s)-tert-butyl 6-(2-(((E)-((Z)-5'-bromo-2'-oxo-[2,3'-biindolinylidene]-3-ylidene) amino)oxy) acetamido)-3-azabicyclo[3.1.0]hexane-3-carboxylate (7q)

Compound 7q was synthesized from compounds 3d and 10b following the procedure described for compound 7a.

Synthesis of tert-butyl ((1R,5S,6s)-3-(2-(((E)-((Z)-5'-bromo-2'-oxo-[2,3'-biindolinylidene]-3-ylidene) amino)oxy) acetyl)-3-azabicyclo[3.1.0]hexan-6-yl) carbamate (7r)

Compound 7r was synthesized from compounds 3d and 10c following the procedure described for compound 7a.

Synthesis of (1R,4R)-tert-butyl 5-(2-(((E)-((Z)-5'-bromo-2'-oxo-[2,3'-biindolinylidene]-3-ylidene) amino)oxy) acetyl)-2,5-diazabicyclo[2.2.1]heptane-2-carboxylate (7s)

Compound 7s was synthesized from compounds 3d and 10d following the procedure described for compound 7a.

Synthesis of (1S,4S)-tert-butyl 5-(2-(((E)-((Z)-5'-bromo-2'-oxo-[2,3'-biindolinylidene]-3-ylidene) amino)oxy) acetyl)-2,5-diazabicyclo[2.2.1]heptane-2-carboxylate (7t)

Compound 7t was synthesized from compounds 3d and 10e following the procedure described for compound 7a.

Example 15: Synthesis of (2Z,3E)-3-((2-oxo-2-(2,6-diazaspiro[3.3]heptan-2-yl) ethoxy)imino)-[2,3'-biindolinylidene]-2'-one (8a)

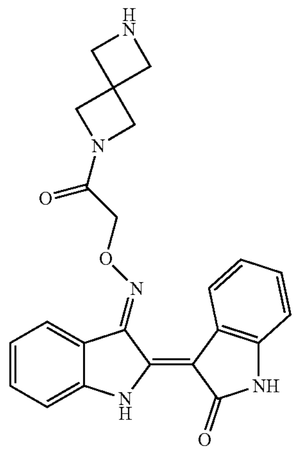 [SMILES: O=C1Nc2ccccc2/C1=C1/Nc2ccccc2/C1=N\OCC(=O)N1CC2(CNC2)C1]

Compound 8a was synthesized from compound 7a following the procedure described for compound 6a.

$^1$H NMR (400 MHZ, DMSO-d$_6$) δ ppm 3.49-3.54 (m, 4H) 4.01 (s, 2H) 4.33 (s, 2H) 5.05 (s, 2H) 6.87-6.93 (m, 2H) 7.02-7.07 (m, 1H) 7.15 (td, J=7.67, 1.14 Hz, 1H) 7.41-7.48 (m, 2H) 8.18-8.21 (m, 1H) 8.42-8.46 (m, 1H). MS (ESI): [M+H]$^+$=415.7.

Example 16: Synthesis of N-((1R,5S,6s)-3-azabicyclo[3.1.0]hexan-6-yl)-2-(((E)-((Z)-2'-oxo-[2,3'-biindolinylidene]-3-ylidene)amino)oxy) acetamide (8b)

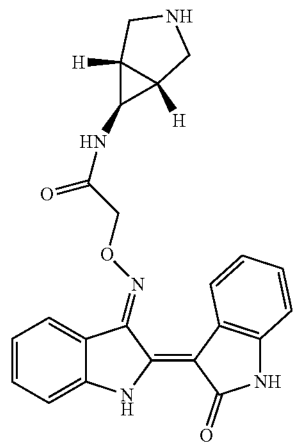

Compound 8b was synthesized from compound 7b following the procedure described for compound 6a.

$^1$H NMR (400 MHZ, DMSO-d$_6$) δ ppm 1.46 (s, 2H) 2.59 (dt, J=4.24, 2.00 Hz, 1H) 2.61 (s, 1H) 2.64 (s, 1H) 2.88 (s, 1H) 2.91 (s, 1H) 4.91 (s, 2H) 6.87-6.90 (m, 1H) 6.93 (td, J=7.67, 1.14 Hz, 1H) 7.01-7.06 (m, 1H) 7.15 (td, J=7.67, 1.14 Hz, 1H) 7.40-7.47 (m, 2H) 8.19 (dt, J=7.61, 1.00 Hz, 1H) 8.29 (d, J=4.12 Hz, 1H) 8.43-8.47 (m, 1H) 10.77 (br. s., 1H) 11.66 (br. s., 1H). MS (ESI): [M+H]$^+$=415.9.

Synthesis of (2Z,3E)-3-((2-((1R,5S,6s)-6-amino-3-azabicyclo[3.1.0]hexan-3-yl)-2-oxoethoxy)imino)-[2,3'-biindolinylidene]-2'-one (8c)

Compound 8c was synthesized from compound 7c following the procedure described for compound 6a.

Example 17: Synthesis of (2Z,3E)-3-((2-((1R,4R)-2,5-diazabicyclo[2.2.1]heptan-2-yl)-2-oxoethoxy) imino)-[2,3'-biindolinylidene]-2'-one (8d)

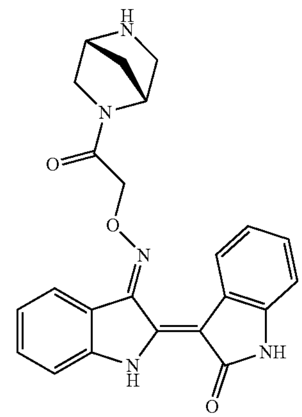

Compound 8d was synthesized from compound 7d following the procedure described for compound 6a.

$^1$H NMR (400 MHZ, DMSO-do, room temperature) 8 ppm 1.54-1.71 (m, 2H) 2.77 (d, J=9.62 Hz, 1H) 2.84 (dt, J=9.79, 2.20 Hz, 1H) 3.16 (d, J=10.76 Hz, 0.5 H) 3.40 (d, J=8.70 Hz, 0.5 H) 3.53 (dd, J=9.04, 2.18 Hz, 0.5 H) 3.58 (s, 0.5 H) 3.68 (s, 0.5 H) 4.64 (d, J=13.97 Hz, 1H) 5.05-5.15 (m, 1H) 5.25 (s, 1H) 6.88 (d, J=7.10 Hz, 1H) 6.93-6.98 (m, 1H) 7.02-7.07 (m, 1H) 7.11-7.17 (m, 1H) 7.40-7.47 (m, 2H) 8.22 (t, J=6.98 Hz, 1H) 8.47 (t, J=8.01 Hz, 1H) 10.76 (br. s., 1H). The $^1$H NMR spectra of 8d at room temperature were doubled for some signals, indicating the presence of two rotational conformers in a ratio of ~1:1 in DMSO-$d_6$. MS (ESI): $[M+H]^+$=415.9.

Synthesis of (2Z,3E)-3-((2-((1S,4S)-2,5-diazabicyclo[2.2.1]heptan-2-yl)-2-oxoethoxy)imino)-[2,3'-biindolinylidene]-2'-one (8e)

Compound 8e was synthesized from compound 7e following the procedure described for compound 6a.

Example 18: Synthesis of (2Z,3E)-5'-fluoro-3-((2-oxo-2-(2,6-diazaspiro[3.3]heptan-2-yl) ethoxy) imino)-[2,3'-biindolinylidene]-2'-one (8f)

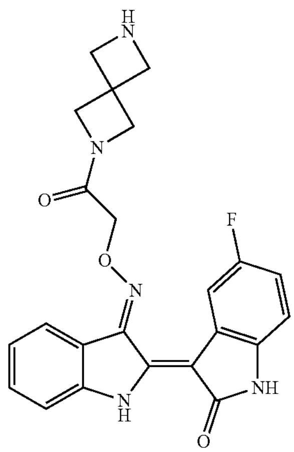 [SMILES: O=C1Nc2ccc(F)cc2/C1=C1/Nc2ccccc2/C1=N\OCC(=O)N1CC2(CNC2)C1]

Compound 8f was synthesized from compound 7f following the procedure described for compound 6a.

$^1$H NMR (400 MHZ, DMSO-$d_6$) δ ppm 3.53 (s, 3H) 3.62 (br. s., 1H) 3.98-4.03 (m, 2H) 4.33 (br. s., 2H) 5.05 (s, 2H) 6.83-6.88 (m, 1H) 6.94-7.00 (m, 1H) 7.07 (td, J=7.27, 1.95 Hz, 1H) 7.42-7.50 (m, 2H) 8.18 (dd, J=7.79, 0.92 Hz, 1H) 8.20-8.25 (m, 1H) 10.80 (br. s., 1H). MS (ESI): $[M+H]^+$=434.6.

Example 19: Synthesis of N-((1R,5S,6s)-3-azabicyclo[3.1.0]hexan-6-yl)-2-(((E)-((Z)-5'-fluoro-2'-oxo-[2,3'-biindolinylidene]-3-ylidene)amino)oxy) acetamide (8g)

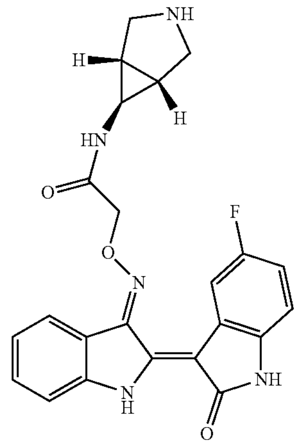

Compound 8g was synthesized from compound 7g following the procedure described for compound 6a.

$^1$H NMR (400 MHZ, DMSO-$d_6$) δ ppm 1.45 (s, 2H) 2.54-2.57 (m, 1H) 2.61 (br. s., 1H) 2.87 (s, 1H) 2.90 (s, 1H) 4.94 (s, 2H) 6.82-6.89 (m, 1H) 6.97 (td, J=8.82, 2.29 Hz, 1H) 7.04-7.10 (m, 1H) 7.42-7.50 (m, 2H) 8.18-8.27 (m, 3H) 10.79 (br. s., 1H) 11.75 (br. s., 1H). MS (ESI): $[M+H]^+$ =434.6.

Synthesis of (2Z,3E)-3-((2-((1R,5S,6s)-6-amino-3-azabicyclo[3.1.0]hexan-3-yl)-2-oxoethoxy)imino)-5'-fluoro-[2,3'-biindolinylidene]-2'-one (8h)

Compound 8 h was synthesized from compound 7 h following the procedure described for compound 6a.

Example 20: Synthesis of (2Z,3E)-3-((2-((1R,4R)-2,5-diazabicyclo[2.2.1]heptan-2-yl)-2-oxoethoxy) imino)-5'-fluoro-[2,3'-biindolinylidene]-2'-one (8i)

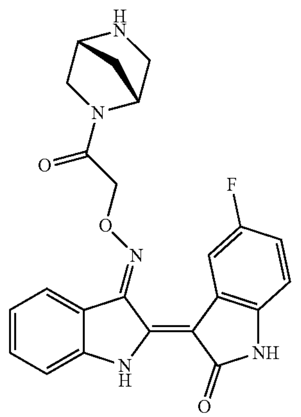

Compound 8i was synthesized from compound 7i following the procedure described for compound 6a.

$^1$H NMR (400 MHZ, DMSO-do, room temperature) 8 ppm 1.55-1.72 (m, 2H) 2.77-2.86 (m, 2H) 3.15-3.19 (m, 0.5

H) 3.53 (dd, J=8.93, 2.06 Hz, 0.5 H) 3.58 (s, 0.5 H) 3.68 (s, 0.5 H) 4.60-4.64 (m, 1H) 5.06-5.17 (m, 1H) 5.23 (d, J=14.88 Hz, 1H) 5.32 (d, J=14.88 Hz, 1H) 6.82-6.87 (m, 1H) 6.92-6.98 (m, 1H) 7.07 (ddd, J=8.01, 6.07, 2.18 Hz, 1H) 7.42-7.50 (m, 2H) 8.21 (dd, J=7.79, 3.43 Hz, 1H) 8.27 (ddd, J=11.22, 6.98, 2.63 Hz, 1H) 10.77 (br. s., 1H) 11.72 (br. s., 1H). The $^1$H NMR spectra of 8i at room temperature were doubled for some signals, indicating the presence of two rotational conformers in a ratio of ~1:1 in DMSO-$d_6$. MS (ESI): $[M+H]^+$=434.6.

Synthesis of (2Z,3E)-3-((2-((1S,4S)-2,5-diazabicyclo[2.2.1]heptan-2-yl)-2-oxoethoxy)imino)-5'-fluoro-[2,3'-biindolinylidene]-2'-one (8j)

Compound 8j was synthesized from compound 7j following the procedure described for compound 6a.

Synthesis of (2Z,3E)-5'-chloro-3-((2-oxo-2-(2,6-diazaspiro[3.3]heptan-2-yl) ethoxy)imino)-[2,3'-biindolinylidene]-2'-one (8k)

Compound 8k was synthesized from compound 7k following the procedure described for compound 6a.

Synthesis of N-((1R,5S,6s)-3-azabicyclo[3.1.0]hexan-6-yl)-2-(((E)-((Z)-5'-chloro-2'-oxo-[2,3'-biindolinylidene]-3-ylidene)amino)oxy) acetamide (81)

Compound 81 was synthesized from compound 71 following the procedure described for compound 6a.

Synthesis of (2Z,3E)-3-((2-((1R,5S,6s)-6-amino-3-azabicyclo[3.1.0]hexan-3-yl)-2-oxoethoxy)imino)-5'-chloro-[2,3'-biindolinylidene]-2'-one (8m)

Compound 8m was synthesized from compound 7m following the procedure described for compound 6a.

Synthesis of (2Z,3E)-3-((2-((1R,4R)-2,5-diazabicyclo[2.2.1]heptan-2-yl)-2-oxoethoxy)imino)-5'-chloro-[2,3'-biindolinylidene]-2'-one (8n)

Compound 8n was synthesized from compound 7n following the procedure described for compound 6a.

Synthesis of (2Z,3E)-3-((2-((1S,4S)-2,5-diazabicyclo[2.2.1]heptan-2-yl)-2-oxoethoxy)imino)-5'-chloro-[2,3'-biindolinylidene]-2'-one (80)

Compound 80 was synthesized from compound 70 following the procedure described for compound 6a.

Synthesis of (2Z,3E)-5'-bromo-3-((2-oxo-2-(2,6-diazaspiro[3.3]heptan-2-yl) ethoxy)imino)-[2,3'-biindolinylidene]-2'-one (8p)

Compound 8p was synthesized from compound 7p following the procedure described for compound 6a.

Synthesis of N-((1R,5S,6s)-3-azabicyclo[3.1.0]hexan-6-yl)-2-(((E)-((Z)-5'-bromo-2'-oxo-[2,3'-biindolinylidene]-3-ylidene)amino)oxy) acetamide (8q)

Compound 8q was synthesized from compound 7q following the procedure described for compound 6a.

Synthesis of (2Z,3E)-3-((2-((1R,5S,6s)-6-amino-3-azabicyclo[3.1.0]hexan-3-yl)-2-oxoethoxy)imino)-5'-bromo-[2,3'-biindolinylidene]-2'-one (8r)

Compound 8r was synthesized from compound 7r following the procedure described for compound 6a.

Synthesis of (2Z,3E)-3-((2-((1R,4R)-2,5-diazabicyclo[2.2.1]heptan-2-yl)-2-oxoethoxy)imino)-5'-bromo-[2,3'-biindolinylidene]-2'-one (8s)

Compound 8s was synthesized from compound 7s following the procedure described for compound 6a.

Synthesis of (2Z,3E)-3-((2-((1S,4S)-2,5-diazabicyclo[2.2.1]heptan-2-yl)-2-oxoethoxy)imino)-5'-bromo-[2,3'-biindolinylidene]-2'-one (8t)

Compound 8t was synthesized from compound 7t following the procedure described for compound 6a.

Synthesis of tert-butyl 6-(2-chloroacetyl)-2,6-diazaspiro[3.3]heptane-2-carboxylate (10a)

TEA (2 eq) was added to a solution of tert-butyl 2,6-diazaspiro[3.3]heptane-2-carboxylate in DCM under argon atmosphere. The reaction mixture was stirred at 0° C. for 10 min. After that, chloroacetyl chloride (1.5 eq) was added dropwise and stirred at 0° C. for 2 hrs. After completion of the reaction monitored by TLC, TLC (chloroform:methanol=20:1, tert-butyl 2,6-diazaspiro[3.3]heptane-2-carboxylate Rf=0.1, product Rf=0.6) showed that tert-butyl 2,6-diazaspiro[3.3]heptane-2-carboxylate was consumed completely and one new spot was detected by ninhydrin staining. After solvent evaporation, the mixture was purified by silica gel column chromatography (eluent: chloroform: methanol=150:1).

Synthesis of (1R,5S,6s)-tert-butyl 6-(2-chloroacetamido)-3-azabicyclo[3.1.0]hexane-3-carboxylate (10b)

Compound 10b was synthesized from chloroacetyl chloride and (1R,5S,6s)-tert-butyl 6-amino-3-azabicyclo[3.1.0]hexane-3-carboxylate following the procedure described for compound 10a.

Synthesis of tert-butyl ((1R,5S,6s)-3-(2-chloroacetyl)-3-azabicyclo[3.1.0]hexan-6-yl) carbamate (10c)

Compound 10c was synthesized from chloroacetyl chloride and tert-butyl ((1R,5S,6s)-3-azabicyclo[3.1.0]hexan-6-yl) carbamate following the procedure described for compound 10a.

Synthesis of (1R,4R)-tert-butyl 5-(2-chloroacetyl)-2,5-diazabicyclo[2.2.1]heptane-2-carboxylate (10d)

Compound 10d was synthesized from chloroacetyl chloride and (1R,4R)-tert-butyl 2,5-diazabicyclo[2.2.1]heptane-2-carboxylate following the procedure described for compound 10a.

Synthesis of (1S,4S)-tert-butyl 5-(2-chloroacetyl)-2,5-diazabicyclo[2.2.1]heptane-2-carboxylate (10e)

Compound 10e was synthesized from chloroacetyl chloride and (1S,4S)-tert-butyl 2,5-diazabicyclo[2.2.1]heptane-2-carboxylate following the procedure described for compound 10a.

Experiment 1. Evaluation of Kinase Inhibition Activity of the Compound According to the Present Invention In this experiment, anti-cancer effect of the compound of the present invention was confirmed by FLT enzyme inhibition test and cell proliferation inhibition test in cancer cell line.

FLT3 activity inhibition was measured by ADP-Glo kinase assay (Promega, cat #V9101). ADP-Glo kinase analysis method is an emission ADP detect method which measures kinase activity by quantification of ADP amount produced during kinase reaction and provides uniform high-throughput screening method.

Analysis performed in two steps. First, after kinase reaction, ADP-Glo™ reagent of equal volume was added to finish kinase reaction, and then the rest ATP was exhausted. Second, Kinase Detection Reagent was added to convert ADP to ATP and newly synthesized ATP was measured by luciferase/luciferin reaction at the same time. Generated light was measured by using luminometer. The measured luminescence amount can be applied to the ATP->ADP standard conversion curve to confirm the correlation with the ADP concentration.

Recombinant proteins containing the FLT3 and FLT3 (D835Y) domains were purchased from Promega (cat #V4064, cat #V4514), respectively. According to the manufacturer's instructions, optimal enzyme, ATP, and substrate concentration were established using the ADP-Glo™ Kinase Assay (Promega, USA). Kinase reaction buffer 5× (200 mM Tris-HCl, pH 7.5, 100 mM $MgCl_2$, 0.5 mg/ml BSA) was diluted and used, and the diluted compound of the present invention (5×, 1 μl), FLT3 enzyme or FLT3/D835Y enzyme (2.5×, 2 μl) and substrate/ATP mixture (2.5×, 2 μl), were mixed sequentially and reacted at room temperature for 120 minutes. Then, ADP-Glo™ Reagent (5 μl) was added and reacted for 40 min at room temperature. Finally, after adding a reagent for detection (Kinase Detection Reagent, 10 μl), reacting at room temperature for 30 min, and then phosphorylation of substrate peptide was measured by measuring luciferase signal (Integration time 0.5-1 second) using SpectraMax ID5 reader (Molecular Devices LLC., San Jose, CA, USA). $IC_{50}$ was calculated by nonlinear regression using Prism version 5.01 (GrapghPad).

Recombinant proteins containing RET wt, RET (M918T) and RET (V804L) domains were purchased from Promega (cat #V8061, cat #VA7274, cat #V4473), respectively. According to the manufacturer's instructions, optimal enzyme, ATP, and substrate concentration were established using ADP-Glo™ Kinase Assay (Promega, USA). Kinase reaction buffer 5× (200 mM Tris-HCl, pH 7.5, 100 mM $MgCl_2$, 0.5 mg/ml BSA) was diluted and used, and the diluted compound of the present invention (5×, 1 μl), FLT3 enzyme or FLT3/D835Y enzyme (2.5×, 2 μl) and substrate/ATP mixture (2.5×, 2 μl) were mixed in order and reacted at room temperature for 120 min. Then, ADP-Glo™ Reagent (5 μl) was added and reacted at room temperature for further 40 min. Lastly, Kinase Detection Reagent (10 μl) was added and reacted for 30 min more at room temperature, and then phosphorylation of substrate peptide was measured by measuring luciferase signal (Integration time 0.5-1 second) using SpectraMax ID5 reader (Molecular Devices LLC., San Jose, CA, USA). $IC_{50}$ was calculated by nonlinear regression using Prism version 5.01 (GrapghPad).

Measured enzyme activity ($IC_{50}$, nM) results are shown in Table 1.

TABLE 1

FLT3 WT/D835Y, RET WT/V804L/M918T kinase inhibition activity assessment

| | Enzyme activity ($IC_{50}$, nM) | | | | |
|---|---|---|---|---|---|
| Example | FLT3 WT | FLT3 D835Y | RET WT | RET V804L | RET M918T |
| 1 (6a) | 1.42 | 0.329 | 1.088 | 1.303 | 0.449 |
| 2 (6b) | 2.49 | 0.524 | 0.964 | 0.553 | 1.249 |
| 3 (6c) | 3.78 | 0.303 | 0.969 | 1.274 | 1.017 |
| 4 (6d) | 1.37 | 0.216 | 0.423 | 0.212 | 0.348 |
| 5 (6e) | 1.57 | 0.135 | 1.851 | 0.851 | 0.771 |
| 6 (6f) | 2.44 | 0.488 | 0.668 | 0.797 | 0.670 |
| 7 (6g) | 1.47 | 0.370 | 1.029 | 0.742 | 0.666 |
| 8 (6h) | 1.355 | 0.303 | 0.441 | 0.540 | 0.344 |
| 9 (6i) | 3.87 | 0.667 | 0.490 | 0.785 | 1.016 |
| 10 (6j) | 2.41 | 0.428 | 0.815 | 0.511 | 0.617 |
| 11 (6n) | 4.57 | 0.553 | 1.715 | 1.017 | 1.275 |
| 12 (5o) | 1.16 | 0.242 | 1.021 | 0.843 | 0.746 |
| 13 (6s) | 4.72 | 0.686 | 1.312 | 0.376 | 1.03 |
| 14 (5t) | 1.17 | 0.423 | 1.025 | 1.544 | 1.262 |
| 15 (8a) | 3.41 | 0.798 | 0.664 | 0.37 | 1.076 |
| 16 (8b) | 3.13 | 0.661 | 0.873 | 0.472 | 1.194 |
| 17 (8d) | 4.24 | 0.552 | 1.53 | 0.904 | 1.438 |
| 18 (8f) | 2.15 | 0.306 | 1.118 | 0.657 | 0.921 |
| 19 (8g) | 3.13 | 0.511 | 1.052 | 0.419 | 1.39 |
| 20 (8i) | 2.94 | 0.271 | 1.882 | 1.04 | 1.194 |

As confirmed from Table 1, the compound of the present invention exhibits a good inhibitory activity against FLT3, FLT3 mutation, RET, and RET mutation.

Experiment 2. Evaluation of Cell Proliferation Inhibition in AML Cell Lines.

Cell proliferation inhibition experiments on acute myeloid leukemia (AML) cell lines tested FLT3 inhibitory activity using MV4-11, Molm-13, and Molm-14 cells, which are FLT3-ITD-expressed AML cell lines. The origin of all cell lines is human-derived cell lines, and the place of purchase and culture conditions of each cell line are as follows.

MV4-11 cells were purchased form the American Type Culture Collection (ATCC, Rockville, MD, USA, cat #CRL-9591), Molm-13 (DSMZ, cat #ACC554), Molm-14 (DSMZ, cat #ACC777), and then cultured in RPMI 1640 medium (Corning Co.10-040-CV) supplemented with 10% fetal bovine serum, 1% penicillin/streptomycin and 4 mM L-glutamine (Life Technology, GrandIsland, NY).

Cell viability was evaluated by Resazurin redox-based analysis method with Alamar Blue Assay Kit (Invitrogen, USA). Specifically, for MV4-11, Molm-13 and Molm-14 cells, 8000 cells were plated on 384-well plates in 45 μl of medium. Compounds were treated with dimethyl sulfoxide (DMSO) as a negative control group. After 3 days (72 hours) of compound addition, 5 μl of Alamar Blue kit reagent was added to each well of 384-well plate and incubated at 37° C. for 2 hours in a humidified $CO_2$ incubator. After incubation, fluorescence density (Flu) was measured at a wavelength of 544 nm and 590 nm using SpectraMax iD3 Multi Mode Microplate Reader (Molecular Devices, ID3-STD). $GI_{50}$ was calculated by nonlinear regression using Prism version 5.01 (GraphPad, LaJolla, CA, USA).

Three types of indirubin compounds disclosed in the prior documents were used as comparative examples.

| | Comparative Example 1 (WO 2014/153023) | Comparative Example 2 (WO 2014/153023) | Comparative Example 3 (WO 2019/088677) |
|---|---|---|---|
| Compound | 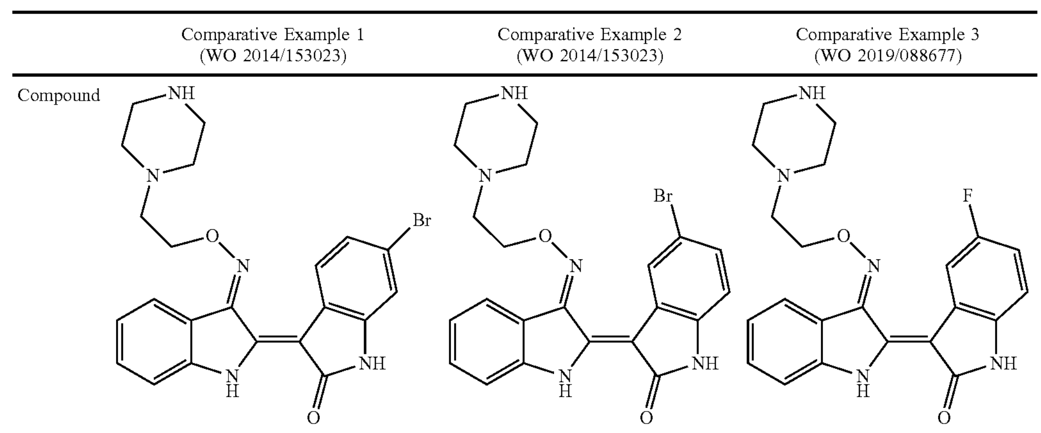 | | |

The measured cell proliferation inhibitory activity ($GI_{50}$, nM) results are shown in Table 2 below.

TABLE 2

| Cell proliferation inhibitory activity in AML cell lines ($GI_{50}$, nM) | | | |
|---|---|---|---|
| | MV4-11 | Molm-13 | Molm-14 |
| Comparative Example 1 | 20 | 11.15 | 9.36 |
| Comparative Example 2 | 7 | 4.08 | 4.08 |
| Comparative Example 3 | 3.7 | 2.53 | 1.6 |
| Example 1 (6a) | 12.36 | — | — |
| Example 2 (6b) | 7.9 | — | — |
| Example 3 (6c) | 90.6 | — | — |
| Example 4 (6d) | 100 fM* | 40 pM** | 30 pM |
| Example 5 (6e) | 0.663 | 1.78 | 1.66 |
| Example 6 (6f) | 15.6 | — | — |
| Example 7 (6g) | 5.65 | — | — |
| Example 8 (6h) | 90.6 | — | — |
| Example 9 (6i) | 0.26 | 500 pM | 470 pM |
| Example 10 (6j) | 0.685 | 1.39 | 1.86 |
| Example 11 (6n) | 40 pM | 162 pM | 100 pM |
| Example 12 (5o) | 4.10 | 5.29 | 6.86 |
| Example 13 (6s) | 61 pM | 200 pM | 170 pM |
| Example 14 (5t) | 3.31 | 5.92 | 7.72 |

TABLE 2-continued

| Cell proliferation inhibitory activity in AML cell lines ($GI_{50}$, nM) | | | |
|---|---|---|---|
| | MV4-11 | Molm-13 | Molm-14 |
| Example 15 (8a) | 100 | — | — |
| Example 16 (8b) | 5.04 | — | — |
| Example 17 (8d) | 0.44 | — | — |
| Example 18 (8f) | 100 | — | — |

TABLE 2-continued

| Cell proliferation inhibitory activity in AML cell lines ($GI_{50}$, nM) | | | |
|---|---|---|---|
| | MV4-11 | Molm-13 | Molm-14 |
| Example 19 (8g) | 6.78 | — | — |
| Example 20 (8i) | 1.32 | — | — |

*fM: femtomolar
**pM: picomolar

As confirmed from Table 2, it was confirmed that the compound of the present invention exhibits strong anti-proliferation activity in acute leukemia cell lines. In particular, it was confirmed that the compounds exhibit strong antiproliferative activity in the FLT3-ITD-expressing MV4-11 cell line expressing the mutant kinase, the FLT3-ITD and RET-expressing Molm-13 cell line, and the FLT3/D835Y and RET-expressing Molm-14 cell line.

Experiment 3. In Vivo Tumor Inhibition Evaluation

Using compound 4 of the present invention and the compound of Comparative Example 3, an in vivo tumor inhibition evaluation was performed on experimental animals. BALB/c nude mice (7-9 weeks old, female, Shanghai Lingchang Biotech Co., LTD.) were used as experimental animals. To enhance tumor development, MV4-11 tumor cells ($10\times10^6$, ATCC-CRL-9591) were inoculated subcutaneously into the right flank of each mouse using 0.2 mL of Matrigel/PBS (1:1) mixture. Animals were randomized and testing started when mean tumor volume reached 100-150 $mm^3$.

Among the randomized animals, a total of 64 animals (8 groups in total, 8 animals in each group) were selected for the tumor inhibition evaluation experiment. The test group of Compound 4 consisted of four groups in total, each of which was a 5 mg/kg administration group, a 10 mg/kg administration group, a 20 mg/kg administration group, and a vehicle administration group. The test group of Comparative Example 3 also consisted of four groups in total, each of which was a 10 mg/kg administration group, a 20 mg/kg administration group, a 40 mg/kg administration group, and a vehicle administration group. Drug was orally administered once a day, and 100% distilled water was used as the excipient.

Weight measurements and tumor inhibition of all subjects were observed for 24 days. Tumor size was measured using calipers, and volume was expressed in $mm^3$.

The results of the comparative experiment with Comparative Example 3 are shown in FIGS. 1a~1d. As confirmed from FIGS. 1a~1d, the compound of the present invention showed no significant change in body weight after administration and exhibited a superior tumor volume reduction tendency compared to the compound of Comparative Example 3. In particular, the tumor inhibition effect in the experiment of administering 5 mg/kg of the compound of the present invention was found to be superior and remarkable compared to the tumor inhibition effect obtained in the experiment of administering 40 mg/kg of the compound of Comparative Example 3.

From this, it was confirmed that the compound of the present invention has excellent inhibitory activity against FLT3 and RET kinases, particularly FLT3 mutant and mutant RET kinases, and an effect of preventing or treating leukemia or lymphoma related thereto.

What is claimed is:

1. A compound or a pharmaceutically acceptable salt thereof, wherein the compound is selected from the group consisting of compounds 5, 9, 10, 11 and 13 below

| COMPOUND | STRUCTURE | NAME |
|---|---|---|
| 4 | 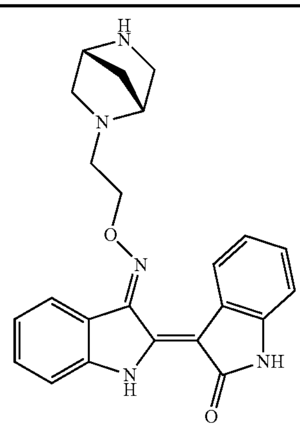 | (2Z,3E)-3-((2-((1R,4R)-2,5-diazabicyclo[2.2.1]heptane-2-yl)ethoxy)imino)-[2,3'-biindolinylidene]-2'-on |
| 5 | 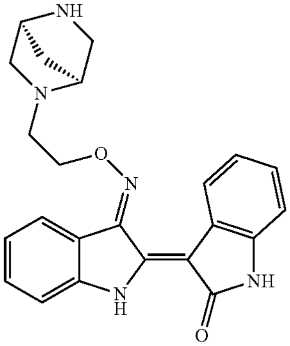 [SMILES: O=C1Nc2ccccc2/C1=C1/Nc2ccccc2/C1=N\OCCN1C[C@@H]2C[C@H]1CN2] | (2Z,3E)-3-((2-((1S,4S)-2,5-diazabicyclo[2.2.1]heptane-2-yl)ethoxy)imino)-[2,3'-biindolinylidene]-2'-on |

-continued

| COMPOUND | STRUCTURE | NAME |
|---|---|---|
| 9 | 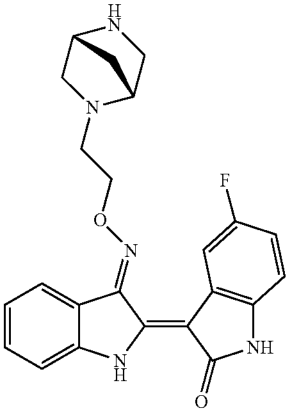 [SMILES: O=C1Nc2ccc(F)cc2/C1=C1/Nc2ccccc2/C1=N\OCCN1C[C@H]2C[C@@H]1CN2] | (2Z,3E)-3-((2-((1R,4R)-2,5-diazabicyclo[2.2.1]heptane-2-yl)ethoxy)imino)-5'-fluoro-[2,3'-biindolinylidene]-2'-on |
| 10 | 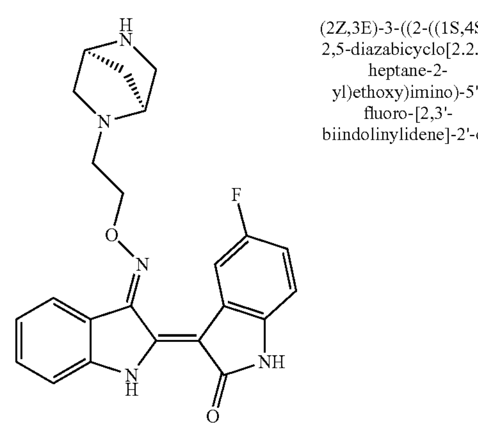 | (2Z,3E)-3-((2-((1S,4S)-2,5-diazabicyclo[2.2.1]heptane-2-yl)ethoxy)imino)-5'-fluoro-[2,3'-biindolinylidene]-2'-on |
| 11 | 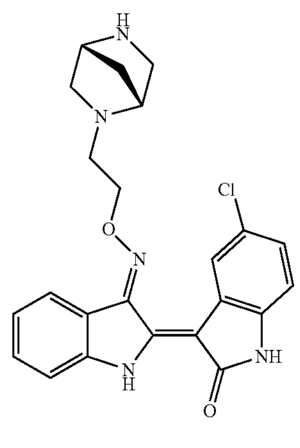 [SMILES: O=C1Nc2ccc(Cl)cc2/C1=C1/Nc2ccccc2/C1=N\OCCN1C[C@H]2C[C@@H]1CN2] | (2Z,3E)-3-((2-((1R,4R)-2,5-diazabicyclo[2.2.1]heptane-2-yl)ethoxy)imino)-5'-chloro-[2,3' -biindolinylidene]-2'-on |

-continued

| COMPOUND | STRUCTURE | NAME |
|---|---|---|
| 13 | 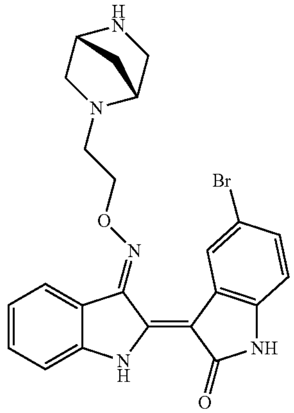 | (2Z,3E)-3-((2-((1R,4R)-2,5-diazabicyclo[2.2.1]heptane-2-yl)ethoxy)imino)-5'-bromo-[2,3'-biindolinylidene]-2'-on. |

2. A pharmaceutical composition for preventing or treating FLT3 and RET-related diseases, comprising the compound or a pharmaceutically acceptable salt thereof of claim 1.

3. The pharmaceutical composition of claim 2, for preventing or treating leukemia or lymphoma.

4. The pharmaceutical composition of claim 2, for preventing or treating multiple myeloma, malignant plasma cell neoplasia, Hodgkin's lymphoma, nodular lymphocyte-predominant Hodgkin's lymphoma, Kahler's disease and myelomatosis, plasma cell leukemia, plasmacytoma, B-cell prolymphocytic leukemia, hairy-cell leukemia, B-Cell Non-Hodgkin's Lymphoma (NHL), Acute Myelogenous Leukemia (AML), Chronic Lymphocytic Leukemia (CLL), Acute Lymphocytic Leukemia (ALL), Chronic Myelogenous Leukemia (CML), Follicular lymphoma, Burkitt's lymphoma, marginal zone lymphoma, mantle cell lymphoma, large cell lymphoma, precursor B-lymphocytic lymphoma, myelogenous leukemia, Waldenstrom's macroglobulinemia, diffuse large B-cell lymphoma, follicular lymphoma, marginal zone lymphoma, mucosal-associated lymphoid tissue Lymphoma, small cell lymphocytic lymphoma, mantle cell lymphoma, Burkitt tumor, primary mediastinal (thymic) large B-cell lymphoma, lymphoplasmacytic lymphoma, Waldenstrom's macroglobulinemia, Lymphatic marginal zone B-cell lymphoma, splenic marginal zone lymphoma, intravascular giant B-Cell Lymphoma, Primary Exudative Lymphoma, Lymphomatous Granulomatosis, T cell/histiocyte-rich large B-cell lymphoma, primary central nervous system lymphoma, primary cutaneous diffuse large B-cell lymphoma (legged type), EBV-positive diffuse large B-cell lymphoma in the elderly, diffuse large B-cell lymphoma related with inflammation, intravascular large B-cell lymphoma, ALK-positive large B-cell lymphoma, plasmacytic lymphoma, large B-cell lymphoma arising from HHV8-associated multicentric Castleman's disease, unclassified B-cell lymphoma with intermediate features between diffuse large B-cell lymphoma and Burkitt's lymphoma, or unclassified B-cell lymphoma with intermediate features between diffuse large B-cell lymphoma and classical Hodgkin's lymphoma.

5. The pharmaceutical composition of claim 4, for preventing or treating acute myeloid leukemia (AML).

6. The pharmaceutical composition of claim 5, wherein the acute myeloid leukemia (AML) expresses mutant FLT3 or mutant RET kinase.

7. A method for preventing or treating FLT3 and RET-related diseases, comprising administering a pharmaceutical composition comprising the compound or a pharmaceutically acceptable salt thereof of claim 1 to a subject in need thereof.

8. The method of claim 7, for preventing or treating leukemia or lymphoma.

9. The method of claim 7, for preventing or treating multiple myeloma, malignant plasma cell neoplasia, Hodgkin's lymphoma, nodular lymphocyte-predominant Hodgkin's lymphoma, Kahler's disease and myelomatosis, plasma cell leukemia, plasmacytoma, B-cell prolymphocytic leukemia, hairy-cell leukemia, B-Cell Non-Hodgkin's Lymphoma (NHL), Acute Myelogenous Leukemia (AML), Chronic Lymphocytic Leukemia (CLL), Acute Lymphocytic Leukemia (ALL), Chronic Myelogenous Leukemia (CML), Follicular lymphoma, Burkitt's lymphoma, marginal zone lymphoma, mantle cell lymphoma, large cell lymphoma, precursor B-lymphocytic lymphoma, myelogenous leukemia, Waldenstrom's macroglobulinemia, diffuse large B-cell lymphoma, follicular lymphoma, marginal zone lymphoma, mucosal-associated lymphoid tissue Lymphoma, small cell lymphocytic lymphoma, mantle cell lymphoma, Burkitt tumor, primary mediastinal (thymic) large B-cell lymphoma, lymphoplasmacytic lymphoma, Waldenstrom's macroglobulinemia, Lymphatic marginal zone B-cell lymphoma, splenic marginal zone lymphoma, intravascular giant B-Cell Lymphoma, Primary Exudative Lymphoma, Lymphomatous Granulomatosis, T cell/histiocyte-rich large B-cell lymphoma, primary central nervous system lymphoma, primary cutaneous diffuse large B-cell lymphoma (legged type), EBV-positive diffuse large B-cell lymphoma in the elderly, diffuse large B-cell lymphoma related with inflammation, intravascular large B-cell lymphoma, ALK-positive large B-cell lymphoma, plasmacytic lymphoma, large B-cell lymphoma arising from HHV8-associated multicentric Castleman's disease, unclassified B-cell lymphoma with intermediate features between diffuse large B-cell lymphoma and Burkitt's lymphoma, or unclassified B-cell lymphoma with intermediate features between diffuse large B-cell lymphoma and classical Hodgkin's lymphoma.

10. The method of claim 9, for preventing or treating acute myeloid leukemia (AML).

11. The method of claim 10, wherein the acute myeloid leukemia (AML) expresses mutant FLT3 or mutant RET kinase.

12. The compound of claim 1, wherein the compound is compound 4.

13. The compound of claim 1, wherein the compound is compound 9.

14. The compound of claim 1, wherein the compound is compound 11.

15. The compound of claim 1, wherein the compound is compound 13.

* * * * *